(12) United States Patent
Ales, III et al.

(10) Patent No.: US 7,355,090 B2
(45) Date of Patent: Apr. 8, 2008

(54) METHOD OF DETECTING THE PRESENCE OF INSULTS IN AN ABSORBENT ARTICLE

(75) Inventors: Thomas M. Ales, III, Neenah, WI (US); Andrew Long, Appleton, WI (US); Meghan E. Collins, Fond du Lac, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 58 days.

(21) Appl. No.: 11/216,977

(22) Filed: Aug. 31, 2005

(65) Prior Publication Data

US 2007/0049883 A1    Mar. 1, 2007

(51) Int. Cl.
*A61F 13/20* (2006.01)
*G08B 13/14* (2006.01)
*G08B 21/00* (2006.01)

(52) U.S. Cl. ............... 604/361; 340/573.5; 340/573.6; 340/604

(58) Field of Classification Search ............... 604/361; 340/573.5, 572.5, 604, 572.4, 573.6, 596
See application file for complete search history.

(56) References Cited

U.S. PATENT DOCUMENTS

| | | | |
|---|---|---|---|
| 3,508,235 A | 4/1970 | Baisden |
| 3,678,928 A | 7/1972 | Mozes |
| 3,778,570 A | 12/1973 | Shuman |
| 4,100,324 A | 7/1978 | Anderson et al. |
| 4,163,449 A | 8/1979 | Regal |
| 4,212,295 A | 7/1980 | Snyder |
| 4,271,406 A | 6/1981 | Wilson |
| 4,347,503 A | 8/1982 | Uyehara |
| 4,356,479 A | 10/1982 | Wilson |
| 4,356,818 A | 11/1982 | Macias et al. |
| 4,539,559 A | 9/1985 | Kelly |
| 4,704,108 A | 11/1987 | Okada |
| 4,704,116 A | 11/1987 | Enloe |
| 4,738,260 A | 4/1988 | Brown |
| 4,754,264 A | 6/1988 | Okada |
| 4,768,023 A | 8/1988 | Xie |

(Continued)

FOREIGN PATENT DOCUMENTS

DE    19918681    10/2000

(Continued)

OTHER PUBLICATIONS

International Search Report for PCT/US2006/021735, dated Oct. 20, 2006, 3 pages.

*Primary Examiner*—Jacqueline Stephens
(74) *Attorney, Agent, or Firm*—Armstrong Teasdale, LLP

(57) ABSTRACT

A method of determining the presence of an insult in an absorbent article is disclosed. The amount of time that elapses between the activation of an alarm and the determination of the presence of a subsequent insult is determined. This elapsed time is compared to a time threshold value and either an insult alarm or a saturation alarm is activated as a function of the comparison. After activation of the alarm for an alarm period, the electrical property of the article is determined at a second time occurring at least a preset period after the end of the alarm period to allow the electrical property to stabilize before determining the electrical property.

14 Claims, 24 Drawing Sheets

U.S. PATENT DOCUMENTS

| | | |
|---|---|---|
| 4,796,014 A | 1/1989 | Chia |
| 4,800,370 A | 1/1989 | Vetecnik |
| 4,940,464 A | 7/1990 | Van Gompel et al. |
| 4,977,906 A | 12/1990 | Di Scipio |
| 5,036,859 A | 8/1991 | Brown |
| 5,043,704 A | 8/1991 | Blakeney |
| 5,114,781 A | 5/1992 | Morman |
| 5,116,662 A | 5/1992 | Morman |
| 5,121,630 A | 6/1992 | Calvin |
| 5,137,033 A | 8/1992 | Norton |
| 5,144,284 A | 9/1992 | Hammett |
| 5,174,656 A | 12/1992 | Dotan |
| 5,264,830 A | 11/1993 | Kline et al. |
| 5,266,928 A | 11/1993 | Johnson |
| 5,284,703 A | 2/1994 | Everhart et al. |
| 5,291,181 A | 3/1994 | DePonte |
| 5,341,127 A | 8/1994 | Smith |
| 5,350,624 A | 9/1994 | Georger et al. |
| 5,392,032 A | 2/1995 | Kline et al. |
| 5,395,358 A | 3/1995 | Lu |
| 5,416,469 A | 5/1995 | Colling |
| 5,459,452 A | 10/1995 | DePonte |
| 5,469,145 A | 11/1995 | Johnson |
| 5,469,146 A | 11/1995 | Gurler |
| 5,486,166 A | 1/1996 | Bishop et al. |
| 5,490,846 A | 2/1996 | Ellis et al. |
| 5,537,095 A | 7/1996 | Dick et al. |
| 5,568,128 A | 10/1996 | Nair |
| 5,570,082 A | 10/1996 | Mahgerefteh et al. |
| 5,645,542 A | 7/1997 | Anjur et al. |
| 5,709,222 A | 1/1998 | Davallou |
| 5,760,694 A | 6/1998 | Nissim |
| 5,766,389 A | 6/1998 | Brandon et al. |
| 5,790,035 A | 8/1998 | Ho |
| 5,796,345 A | 8/1998 | Leventis et al. |
| 5,802,611 A | 9/1998 | McKenzie |
| 5,808,554 A | 9/1998 | Shuminov |
| 5,817,076 A | 10/1998 | Fard |
| 5,820,973 A | 10/1998 | Dodge, II et al. |
| 5,838,240 A | 11/1998 | Johnson |
| 5,844,862 A | 12/1998 | Cocatre-Zilgien |
| 5,868,723 A | 2/1999 | Al-Sabah |
| 5,881,731 A | 3/1999 | Remes |
| 5,883,028 A | 3/1999 | Morman et al. |
| 5,903,222 A | 5/1999 | Kawarizadch |
| 5,904,671 A | 5/1999 | Navot |
| 5,959,535 A | 9/1999 | Remsburg |
| 5,964,743 A | 10/1999 | Abuto et al. |
| 6,093,869 A | 7/2000 | Roe |
| 6,097,297 A | 8/2000 | Fard |
| 6,101,366 A | 8/2000 | Castillo |
| 6,135,945 A | 10/2000 | Sultan |
| 6,149,636 A | 11/2000 | Roe |
| 6,160,198 A | 12/2000 | Roe |
| 6,163,262 A | 12/2000 | Wu |
| 6,186,991 B1 | 2/2001 | Roe |
| 6,231,557 B1 | 5/2001 | Krautkramer et al. |
| 6,246,330 B1 | 6/2001 | Nielsen |
| 6,348,640 B1 | 2/2002 | Navot |
| 6,362,389 B1 | 3/2002 | McDowall et al. |
| 6,373,395 B1 | 4/2002 | Kimsey |
| 6,384,296 B1 | 5/2002 | Roe |
| 6,384,728 B1 | 5/2002 | Kanor |
| 6,544,200 B1 | 4/2003 | Smith |
| 6,552,245 B1 | 4/2003 | Roessler et al. |
| 6,583,722 B2 | 6/2003 | Jeutter et al. |
| 6,603,403 B2 | 8/2003 | Jeutter et al. |
| 6,645,190 B1 | 11/2003 | Olson et al. |
| 6,755,795 B2 | 6/2004 | Marmaropoulos |
| 6,756,521 B1 | 6/2004 | Breitkopf |
| 6,772,454 B1 | 8/2004 | Barry et al. |
| 6,772,708 B2 | 8/2004 | Klofta et al. |
| 6,774,800 B2 | 8/2004 | Friedman et al. |
| 6,970,091 B2 | 11/2005 | Roe |
| 2002/0070868 A1 | 6/2002 | Jeutter et al. |
| 2002/0145525 A1 | 10/2002 | Friedman et al. |
| 2002/0145526 A1 | 10/2002 | Friedman et al. |
| 2004/0106202 A1 | 6/2004 | Zainiev |
| 2004/0113801 A1 | 6/2004 | Gustafson |
| 2004/0131651 A1 | 7/2004 | Panero et al. |
| 2004/0138546 A1 | 7/2004 | Reho et al. |
| 2004/0138723 A1 | 7/2004 | Malick et al. |
| 2004/0140897 A1 | 7/2004 | Fabre et al. |
| 2005/0146436 A1 | 7/2005 | Roe |

FOREIGN PATENT DOCUMENTS

| | | |
|---|---|---|
| DE | 19939902 | 3/2001 |
| DE | 19937779 | 2/2002 |
| GB | 2321990 | 8/1998 |
| JP | 09033468 A | 2/1997 |
| WO | 9742613 A2 | 11/1997 |
| WO | WO 00/37009 | 6/2000 |
| WO | WO 02/47592 | 6/2002 |
| WO | WO 02/48983 | 6/2002 |
| WO | WO 03/051254 | 6/2003 |
| WO | WO 2004021944 | 3/2004 |
| WO | WO 2004028429 | 4/2004 |

METHOD OF DETECTING THE PRESENCE OF INSULTS IN AN ABSORBENT ARTICLE

BACKGROUND OF THE INVENTION

The present invention relates generally to a method of detecting the presence of an insult in an absorbent article while it is being worn by a wearer.

Disposable absorbent articles find widespread use as personal care products such as diapers, children's toilet training pants and other infant and child care products, adult incontinence garments and other adult care products, sanitary napkins and other feminine care products and the like, as well as surgical bandages and sponges and medical garments. These articles absorb and contain body waste and are intended to be discarded after a limited period of use; i.e., the articles are not intended to be laundered or otherwise restored for reuse. Conventional disposable absorbent articles comprise an absorbent body disposed between an inner layer adapted for contacting the wearer's skin and an outer layer for inhibiting liquid waste absorbed by the absorbent body from leaking out of the article. The inner layer of the absorbent article is typically liquid permeable to permit body waste to pass therethrough for absorption by the absorbent body.

Disposable absorbent training pants, in particular, are useful in toilet training children. Typically, these disposable undergarments are similar to washable, cloth underwear in the manner in which they are put on and worn, yet provide an absorbent function similar to diapers to maintain skin health. Training pants provide a child undergoing toilet training with an undergarment that eases the transition from diapers to washable, cloth underwear as they become more confident in their ability to use the toilet independently.

In order to learn to use the toilet independently, a child must first learn to recognize when urination has occurred. Because urination may often occur during an activity that distracts the child to the extent that the child does not notice urination, this recognition can represent a substantial hurdle in the training process. Also, a child's ability to recognize when urination occurs may be hampered by the improved performance of disposable absorbent undergarments which quickly draw and retain urine away from the wearer's skin after an insult occurs.

Close monitoring of a toilet-training child by a caregiver can be helpful in that when urination occurs it can be discussed by the child and caregiver to enhance and improve the learning experience. Therefore, it is beneficial to provide the caregiver with immediate notification and/or verification that urination has occurred so that it may be discussed with the child while the event is still fresh in the child's mind.

One way of monitoring a toilet-training child is by using a system that detects a change in an electrical property of the undergarment which electrical property is a function of the wetness of the undergarment. For example, the electrical property may be resistance, conductance, impedance, capacitance or any other parameter which varies as the wetness of the undergarment varies. For example, pair of spaced apart parallel conductors may be situated within the absorbent material of the undergarment. These conductors are in electrical contact with the absorbent material of the undergarment and are connected to a sensing circuit for monitoring the electrical property, the circuit includes a power source, such as a battery. For example, the circuit may comprise a voltage divider for detecting resistance between the conductors. The output of the circuit is an analog output voltage that corresponds to a resistance value. When the undergarment is dry, the resistance between the conductors is extremely high and relatively infinite, appearing as an open circuit. When the undergarment is wet, more particularly when the absorbent material of the undergarment between the conductors becomes wet, the resistance of the undergarment at that area drops to a relatively lower value because urine acts as a conductor.

Accordingly, in a conventional system a sensor monitors the resistance between the conductors and compares resistance values to a predetermined and fixed threshold resistance value. If a resistance value is less than the threshold resistance value, then the sensing circuit (herein sensor) sends a signal to an alarm device, which informs the caregiver and/or the wearer that the wearer has urinated. For example, the alarm device may be a device for producing an auditory signal, such as a song, a visual signal, such as a light, or a tactile signal, such as a change in temperature.

These conventional devices may be prone to giving false positives, that is informing the caregiver and/or the user that there is urination present in the undergarment when there is not because there is only one "check" or "test" for the presence of urination (i.e., whether the resistance of the undergarment falls below a fixed threshold value). There are situations, such as when the child sits or other pressure is applied to an undergarment that has been previously insulted, when the resistance of the undergarment may fall below the threshold value, thus indicating a new insult, when in fact a subsequent insult has not occurred (i.e., detecting a false-positive). Accordingly, conventional devices may be ill-suited for accurately detecting multiple insults and/or preventing the detection of false-positives. Moreover, sweat may at least somewhat saturate the undergarment, typically over a relative lengthy period of time, and may trigger the sensor. Moreover still, after a first insult of urination by the wearer, the resistance value of the undergarment is substantially less than when the product was dry. However, the threshold value has not changed, and therefore, the resistance may be lower than the threshold, thus triggering an alarm, even though a subsequent insult has not occurred.

SUMMARY OF THE INVENTION

In general, a method according to one embodiment of the present invention for detecting and communicating to a caregiver and/or the wearer the presence of an insult within the absorbent article comprises monitoring an electrical property of the article as the article is being worn by the wearer. The electrical property at a first time is determined and expressed as a first indicator value. The insult alarm is activated to inform the caregiver and/or the wearer of the presence of an insult in the article when the first indicator value is indicative of an insult. The electrical property of the article is determined after activating the insult alarm. The electrical property is expressed as a second indicator value. The second indicator value is determined to be indicative of the presence of a second insult within the article. The amount of time that elapsed between the activation of the alarm and the determination of the indication of the presence of the second insult is determined. The elapsed time is compared to a time threshold value and either an insult alarm or a saturation alarm is activated as a function of the comparison.

In another embodiment, the method comprises monitoring an electrical property of the article at a first time and expressing the electrical property as a first indicator value. An insult alarm is activated for an alarm period to inform the caregiver and/or the wearer of the presence of a first insult in the article when the first indicator value is indicative of an insult. The electrical property of the article is determined at a second time occurring at least a preset period after the end of the alarm period. The preset period allows the electrical property to stabilize. The electrical property is expressed as a second indicator value. The insult alarm is activated to inform the caregiver and/or the wearer of the presence of a second insult in the article when the second indicator value is indicative of an insult.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
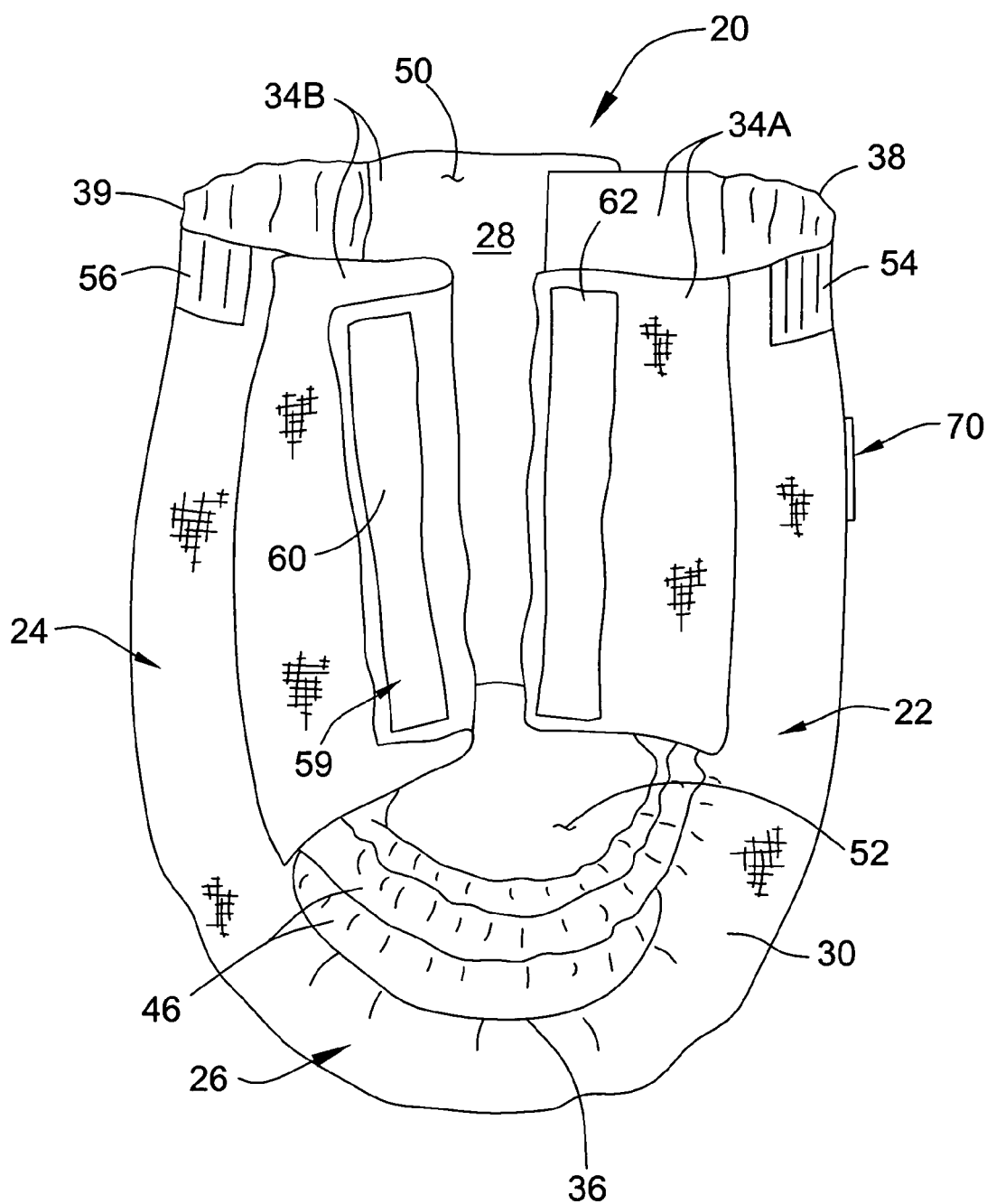
FIG. 1 is a side perspective of an article of the present invention shown in the form of a pair of training pants having a mechanical fastening system fastened on one side of the training pants and unfastened on the opposite side thereof.

Referring now to the drawings and in particular to FIG. 1, an absorbent article of the present invention is representatively illustrated therein in the form of children's toilet training pants and is indicated in its entirety by the reference numeral 20. The absorbent article 20 may or may not be disposable, which refers to articles that are intended to be discarded after a limited period of use instead of being laundered or otherwise conditioned for reuse. It is understood that the present invention is suitable for use with various other absorbent articles intended for personal wear, including but not limited to diapers, feminine hygiene products, incontinence products, medical garments, surgical pads and bandages, other personal care or health care garments, and the like without departing from the scope of the present invention.

By way of illustration only, various materials and methods for constructing training pants such as the pants 20 of the various aspects of the present invention are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference.

Figure 4:
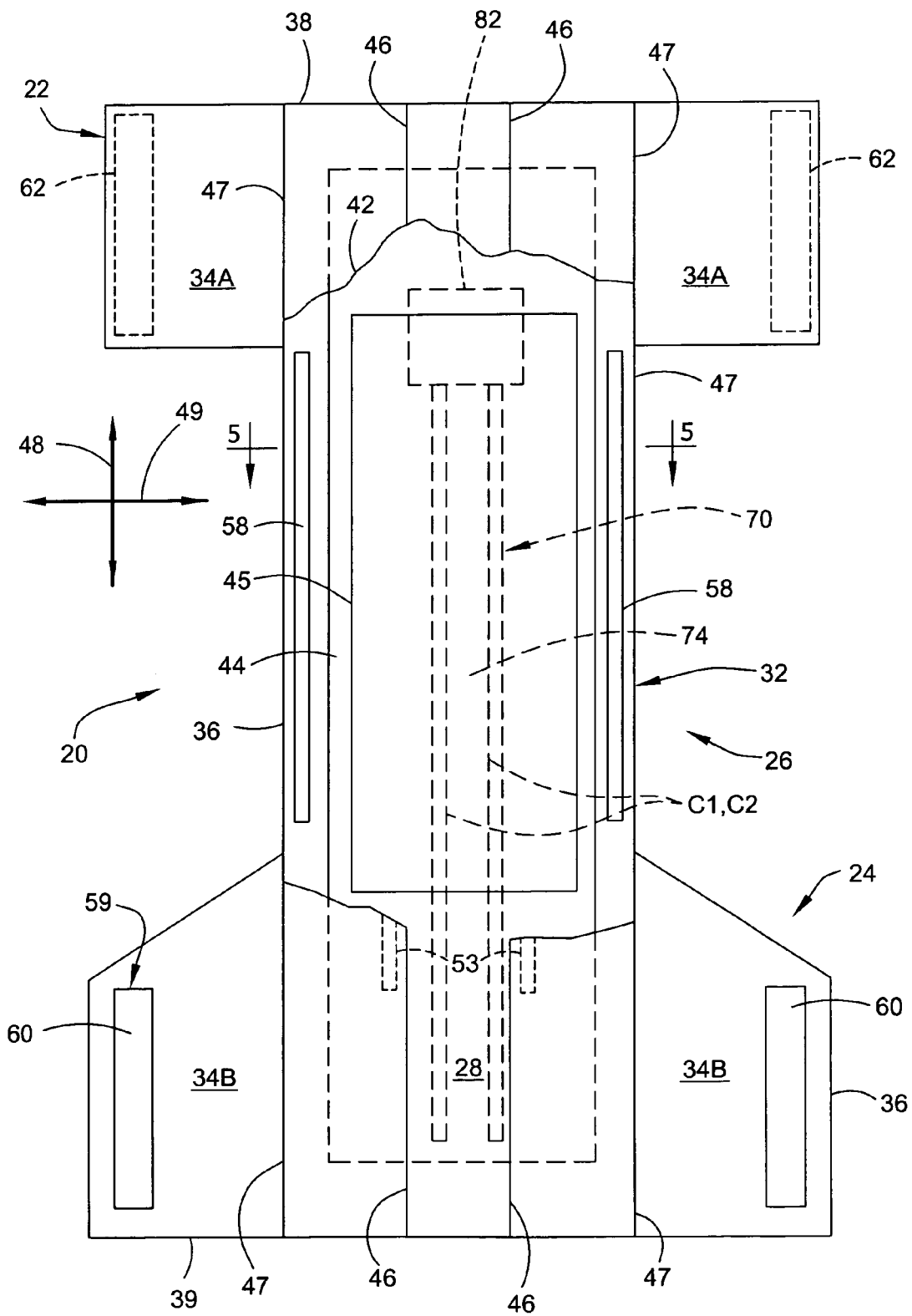
FIG. 4 is a top plan view of the training pants of FIG. 1 with the pants in an unfastened, unfolded and laid flat condition, and showing the surface of the training pants that that faces the wearer when worn and with portions cut away to show underlying features.

The pair of training pants 20 is illustrated in FIG. 1 in a partially fastened condition. The pants 20 define a longitudinal direction 48 of the pants and a lateral direction 49 thereof perpendicular to the longitudinal direction as shown in FIG. 4. The pants 20 further define a pair of longitudinal end regions, otherwise referred to herein as a front waist region, generally indicated at 22, and a back waist region, generally indicated at 24, and a center region, otherwise referred to herein as a crotch region, generally indicated at 26, extending longitudinally between and interconnecting the front and back waist regions 22, 24. The front and back waist regions 22, 24 comprise those portions of the pants 20, which when worn, wholly or partially cover or encircle the waist or mid-lower torso of the wearer. The crotch region 26 generally is that portion of the pants 20 which, when worn, is positioned between the legs of the wearer and covers the lower torso and crotch of the wearer. The pants 20 also define an inner surface 28 that faces toward the wearer when the pants are being worn, and an outer surface 30 opposite the inner surface. With additional reference to FIG. 4, the pair of training pants 20 has a pair of laterally opposite side edges 36 and a pair of longitudinally opposite waist edges (broadly, longitudinal ends), respectively designated front waist edge 38 and back waist edge 39.

In the embodiment of FIGS. 1-4, the training pants 20 comprise a generally rectangular central absorbent assembly, generally indicated at 32, and side panels 34A, 34B formed separately from and secured to the central absorbent assembly. The side panels 34A, 34B are permanently bonded along seams to the central absorbent assembly 32 in the respective front and back waist regions 22 and 24 of the pants 20. More particularly, the front side panels 34A can be permanently bonded to and extend transversely outward beyond side margins 47 of the absorbent assembly 32 at the front waist region 22, and the back side panels 34B can be permanently bonded to and extend transversely outward beyond the side margins of the absorbent assembly at the back waist region 24. The side panels 34A and 34B may be bonded to the absorbent assembly 32 using attachment means known to those skilled in the art such as adhesive, thermal or ultrasonic bonding.

The front and back side panels 34A and 34B, upon wearing of the pants 20, thus comprise the portions of the training pants 20 which are positioned on the hips of the wearer. The front and back side panels 34A and 34B can be permanently bonded together to form the three-dimensional configuration of the pants 20, or be releasably connected with one another such as by a fastening system 59 of the illustrated aspects. As is known in the art, the side panels 34A, 34B may comprise elastic material or stretchable but inelastic materials.

Figure 2:
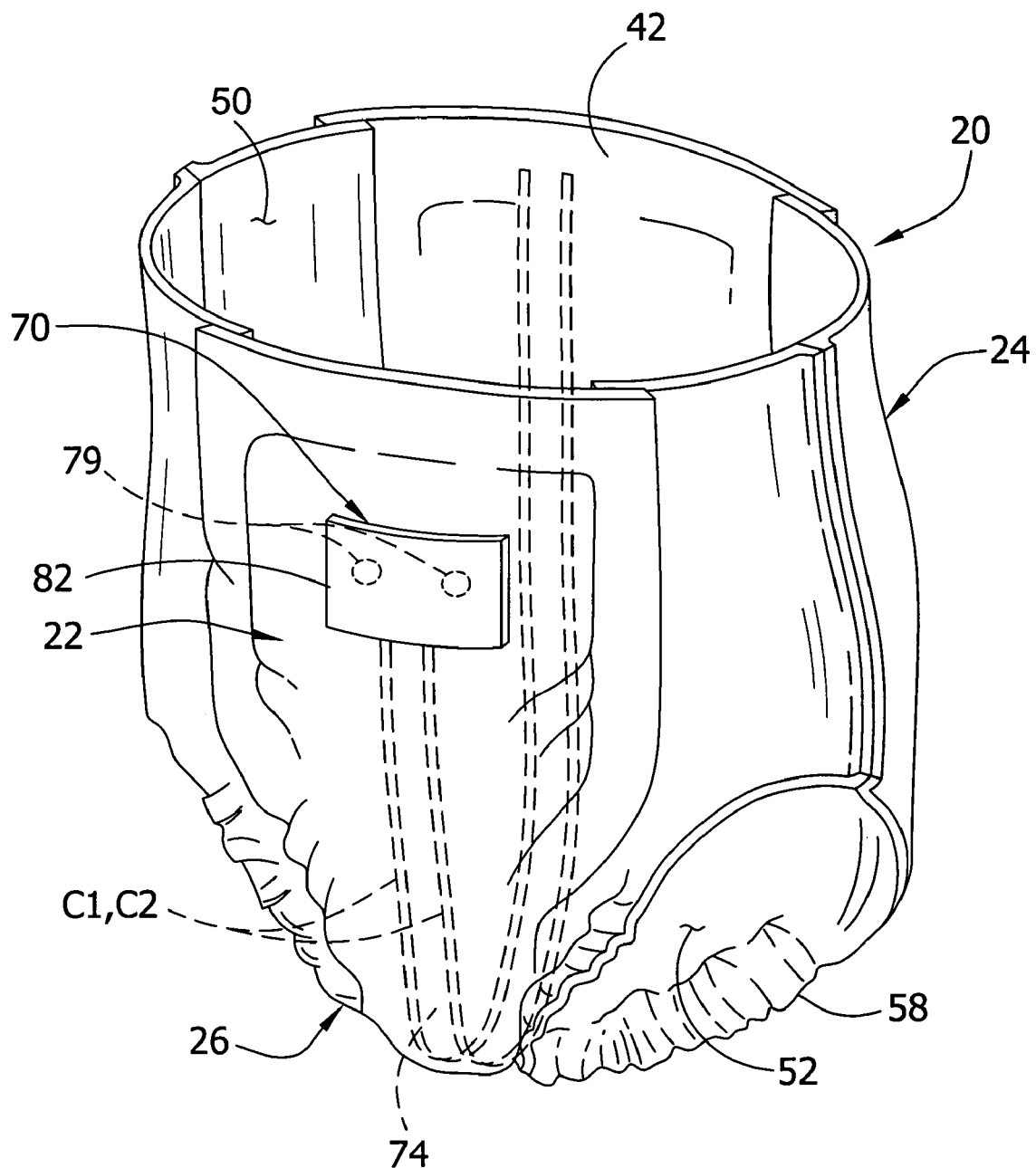
FIG. 2 is a perspective view of the pants of FIG. 1.
Figure 3:
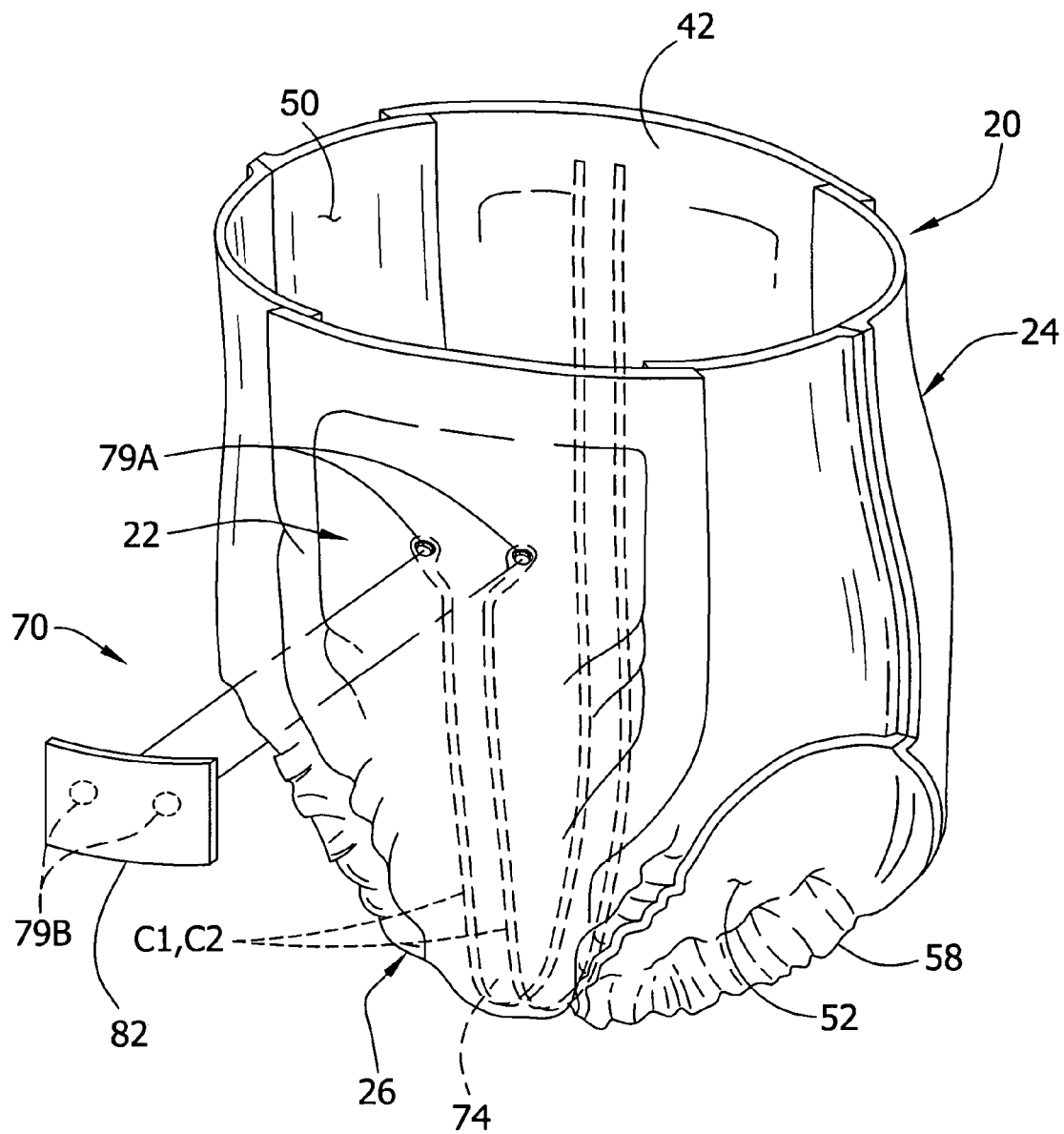
FIG. 3 is a perspective view of the pants similar to FIG. 2 showing a housing of a monitoring system removed from the article.

The absorbent assembly 32 is illustrated in FIGS. 1-3 as having a rectangular shape. However, it is contemplated that the absorbent assembly 32 may have other shapes (e.g., hourglass, T-shaped, I-shaped, and the like) without departing from the scope of this invention. It is also understood that the side panels 34A, 34B may instead be formed integrally with the absorbent assembly 32 without departing from the scope of this invention.

Figure 5:
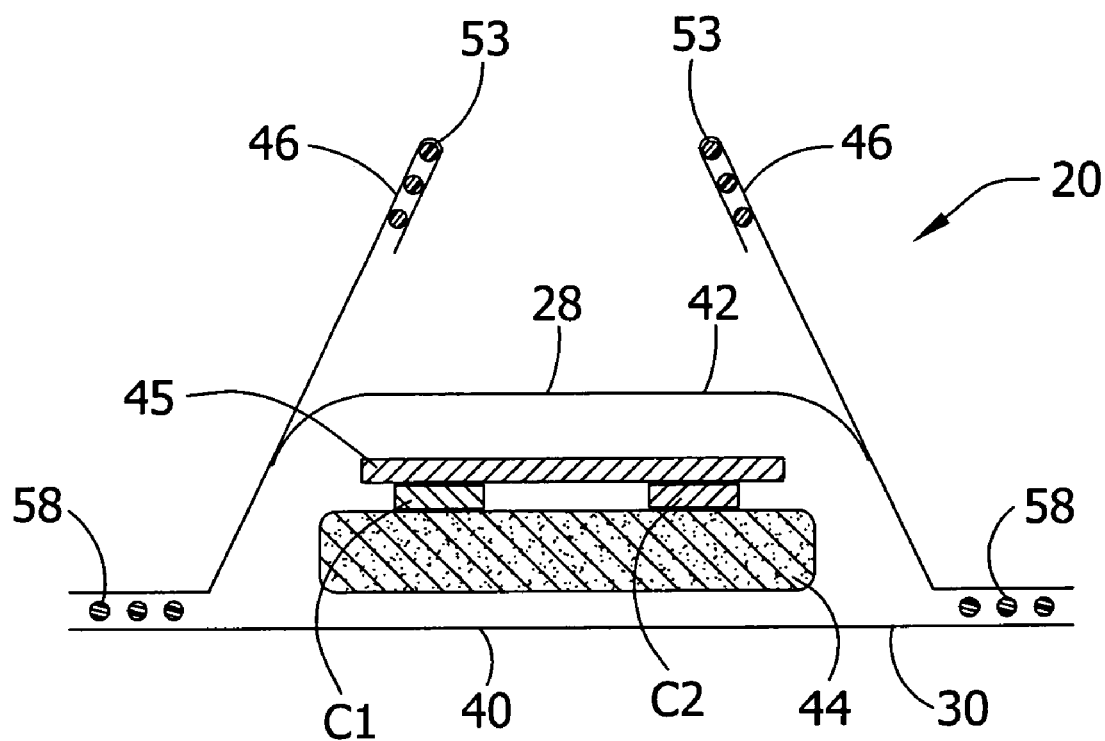
FIG. 5 is cross-sectional view of the pants taken along the plane including line 5-5 of FIG. 4.

As shown best in FIGS. 4 and 5, the absorbent assembly 32 comprises an outer cover 40 and a bodyside liner 42 attached to the outer cover 40 in a superposed (opposed) relation therewith by adhesives, ultrasonic bonds, thermal bonds, pressure bonds, or other conventional techniques.

The liner 42 is suitably joined to the outer cover 40 along at least a portion of the longitudinal ends of the pants 20. In addition, the liner 42 is suitably joined to the outer cover 40. The liner 42 is suitably adapted, i.e., positioned relative to the other components of the pants 20, for contiguous relationship with the wearer's skin during wear of the pants. The absorbent assembly 32 also comprises an absorbent structure 44 disposed between the outer cover 40 and the bodyside liner 42 for absorbing liquid body exudates exuded by the wearer and a surge management layer 45 disposed between the absorbent structure and the bodyside liner. A pair of containment flaps 46 are secured to the bodyside liner 42 for inhibiting the lateral flow of body exudates.

With the training pants 20 in the fastened position as partially illustrated in FIG. 1, the front and back waist regions are connected together by the fastening system 48 to define the three-dimensional pants configuration having a waist opening 50 and a pair of leg openings 52. The front and back waist edges 38 and 39 (e.g., longitudinal ends) of the training pants 20 are configured to encircle the waist of the wearer to define the waist opening 50 (FIG. 1) of the pants.

As illustrated in FIG. 4, a flap elastic member 53 can be operatively joined with each containment flap 46 in any suitable manner as is well known in the art. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 may comprise a front waist elastic member 54 (FIG. 1), a rear waist elastic member 56, and leg elastic members 58 (FIGS. 2-4), as are known to those skilled in the art. The flap elastic members 53, the waist elastic members 54 and 56, and the leg elastic members 58 can be formed of any suitable elastic material that is well known to those skilled in the art.

The fastening system 80 of the illustrated embodiment comprises laterally opposite first fastening components 60 adapted for refastenable engagement to corresponding laterally opposite second fastening components 62. In one embodiment, a front or outer surface of each of the fastening components 60, 62 comprises a plurality of engaging elements. The engaging elements of the first fastening components 60 are adapted to repeatedly engage and disengage corresponding engaging elements of the second fastening components 62 to releasably secure the pants 20 in its three-dimensional configuration. The fastening components 60, 62 can comprise any refastenable fasteners suitable for absorbent articles, such as adhesive fasteners, cohesive fasteners, mechanical fasteners, or the like. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

The outer cover 40 suitably comprises a material that is substantially liquid impermeable. The outer cover 40 may comprise a single layer of liquid impermeable material, or more suitably comprise a multi-layered laminate structure in which at least one of the layers is liquid impermeable. While it is not a necessity for the outer layer to be liquid permeable, it is suitable that it provides a relatively cloth-like texture to the wearer. Alternatively, the outer cover 40 may comprise a woven or non-woven fibrous web layer that has been totally or partially constructed or treated to impart the desired levels of liquid impermeability to selected regions that are adjacent or proximate the absorbent structure. The outer cover 40 may also be stretchable, and in some embodiments it may be elastomeric. Reference is made to U.S. Pat. No. 5,883,028, issued to Morman et al., U.S. Pat. No. 5,116,662 issued to Morman and U.S. Pat. No. 5,114,781 issued to Morman, all of which are hereby incorporated herein by reference, for additional information regarding suitable outer cover materials.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. The bodyside liner 42 may also be stretchable, and in some embodiments it may be elastomeric. Reference is made to U.S. patent application Ser. No. 09/563,417 filed on May 3, 2000 by Roessler et al., U.S. patent application Ser. No. 09/698,512 filed on Oct. 27, 2000 by Vukos et al., both of which are incorporated by reference herein, for additional information regarding bodyside liner material.

The absorbent structure 44 is disposed between the outer cover 40 and the bodyside liner 42, which can be joined together by any suitable means such as adhesives, ultrasonic bonds, thermal bonds, or the like. While the illustrated absorbent structure 44 is shown and described herein as extending from the crotch region 26 into both the front and back waist regions 22 and 24, it is contemplated that the absorbent structure may extend from the crotch region into only the front waist region, or only the back waist region, without departing from the scope of this invention.

The absorbent structure 44 is suitably compressible, conformable, non-irritating to a wearer's skin, and capable of absorbing and retaining liquids and certain body wastes. For example, the absorbent structure 44 may comprise cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof.

The materials may be formed into an absorbent web structure by employing various conventional methods and techniques known in the art. For example, the absorbent structure 44 may be formed by a dry-forming technique, an air forming technique, a wet-forming technique, a foam-forming technique, or the like, as well as combinations thereof. Methods and apparatus for carrying out such techniques are well known in the art. The absorbent structure 44 may alternatively comprise a coform material such as the material disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference.

Superabsorbent material is suitably present in the absorbent structure 44 in an amount of from about 0 to about 90 weight percent based on total weight of the absorbent structure. The absorbent structure 44 may suitably have a density within the range of about 0.10 to about 0.35 grams per cubic centimeter. Superabsorbent materials are well known in the art and can be selected from natural, synthetic, and modified natural polymers and materials.

In one embodiment, the absorbent structure 44 may be stretchable so as not to inhibit the stretchability of other components to which the absorbent structure may be adhered, such as the outer cover 40 and bodyside liner 42. For example, the absorbent structure may comprise materials disclosed in U.S. Pat. Nos. 5,964,743, 5,645,542, 6,231, 557, 6,362,389, and international patent application WO 03/051254, the disclosure of each of which is incorporated by reference herein.

The surge management layer 45 may be attached to various components of the article 20 such as the absorbent structure 44 and/or the bodyside liner 42 by methods known in the art, such as by adhesive, ultrasonic or thermal bonding. The surge management layer 45 helps to decelerate and diffuse surges or gushes of liquid that may be rapidly introduced into the absorbent structure 44 of the article 20. Desirably, the surge management layer 45 can rapidly accept and temporarily hold the liquid prior to releasing the liquid into the storage or retention portions of the absorbent structure 44. Examples of suitable surge management layers 45 are described in U.S. Pat. No. 5,486,166; and U.S. Pat. No. 5,490,846. Other suitable surge management materials are described in U.S. Pat. No. 5,820,973. The entire disclosures of these patents are incorporated by reference herein.

Optionally, a substantially liquid permeable. wrapsheet (not shown) may surround the absorbent structure 44 to help maintain the integrity of the absorbent structure 44.

The training pants 20 of the present invention include a wetness monitoring system for detecting the presence of urine (broadly, an insult) within the pants 20. Although the wetness monitoring system may take on other configurations, this particular configuration of the system monitors an electrical characteristic of the pants and determines whether the child has urinated in the pants using such electrical characteristic. After detection of urine, the system informs a caregiver and/or a child of the presence of the urine by generating an insult alarm. The alarm may be, for example, either an auditory signal, such as a song, or a tactile signal, such as temperature change, or a visual signal, such as a blinking light. It is understood that the system may comprise a device for sending a wireless signal to a remote auditory, visual, tactile or other sensory alarm.

In one particularly suitable embodiment, shown best in FIGS. 2-4, one example of the wetness monitoring system is generally indicated by reference numeral 70. The monitoring system 70 includes a sensor for detecting the electrical property (e.g., resistance R) of the article. The sensor includes a pair of spaced apart generally parallel conductors C1, C2 disposed within the pants 20 that define a monitoring area 74 of the pants disposed between the conductors. The conductors C1, C2 may be constructed of any material that is generally electrically conductive. For example, the conductors may be constructed of metal strips (e.g., aluminum strips), metal films, coated films, conductive polymers, conductive inks, or conductive threads. Other conductors are within the scope of this invention. The conductors C1, C2 extend longitudinally from the front waist region 22, through the crotch region 26, to the back waist region 24 of the pants 20. As shown best in FIG. 5, the conductors C1, C2 are disposed within the absorbent assembly 32 between the absorbent structure 44 and the surge management layer 45, although the conductors may be disposed at other locations without departing from the scope of this invention.

Figure 6:
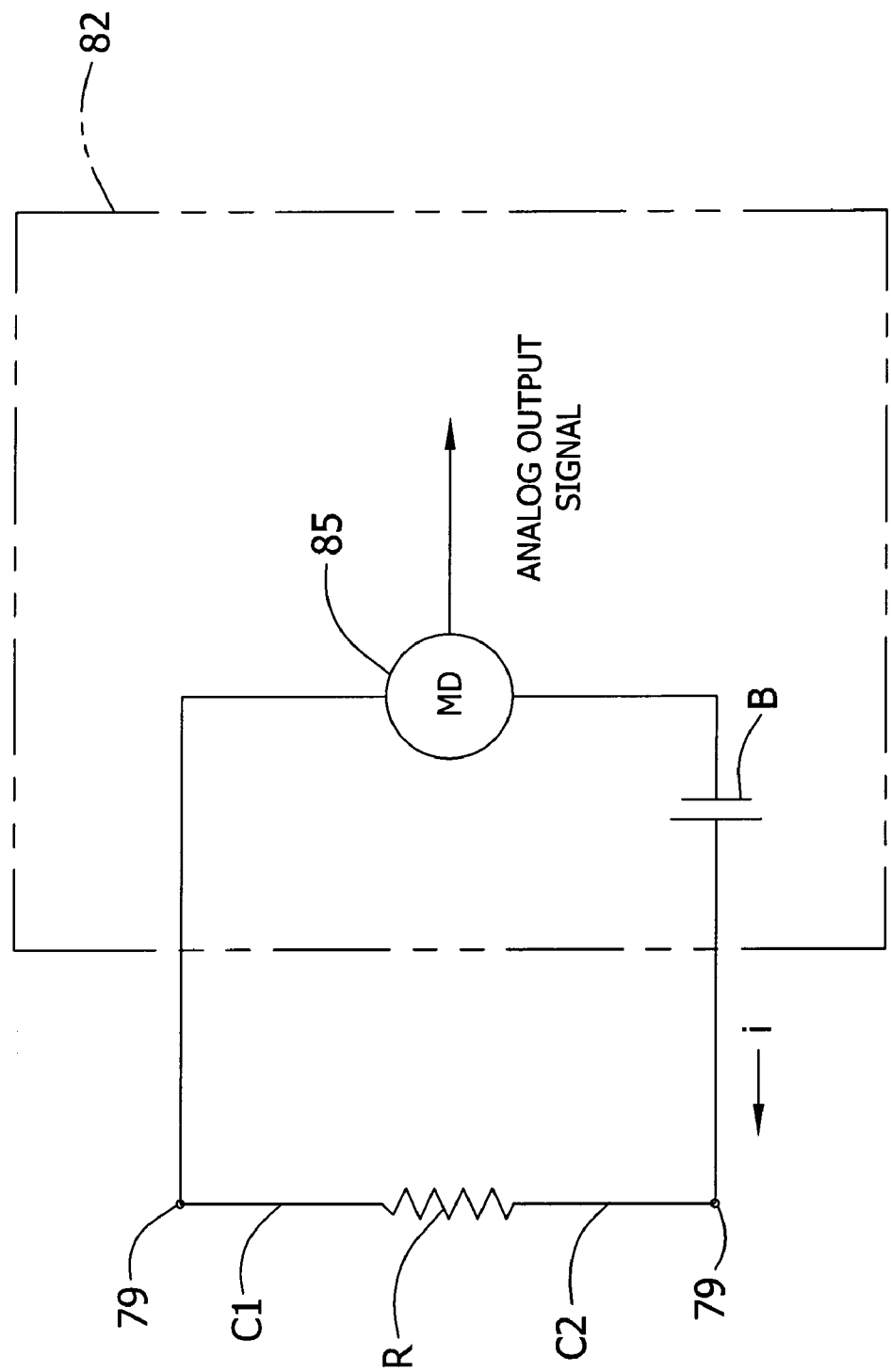
FIG. 6 is a schematic illustration of the pants and one embodiment of a monitoring system of the present invention.

Current i from a current source B (illustrated schematically in FIG. 6) runs through the conductors C1, C2 of the sensor. The current source i may be a direct current source such as a battery (as illustrated), or an alternating current source. In the illustrated embodiment, the conductors C1, C2 are electrically connected to the current source by way of electrically conductive snap fasteners 79. Other ways of electrically connecting the conductors to the current source are within the scope of this invention. As illustrated in FIG. 3, each corresponding end of each conductor C1, C2 is connected to a first snap fastener member 79A located in the front waist region 22 of the pants 20. Alternatively, the first snap fastener member may be located in the back waist region 24, or other locations on the pants 20. A housing 82 that houses the current source i has corresponding second snap fastener elements 79B for engaging the first snap fasteners 79A and securing the housing to the pants 20. In addition to the current source i, the housing 82 of the present embodiment also houses the remaining components of the wetness monitoring system 70 that will be described hereinafter, although it is contemplated that the housing may include only some or none of the remaining components. In the illustrated embodiment the housing 82 is releasably secured to the pants 20 by way of the snap fasteners 79, although it is understood that the housing may be permanently secured to the pants without departing from the scope of this invention.

A measuring device 85 (FIG. 6) of the sensor measures an electrical property of the monitoring area 74 of the pants 20. In one embodiment, the resistance R of the monitoring area 74 of the pants 20 is measured. Because the conductors C1, C2 are spaced apart, current from the current source i must pass through the monitoring area 74 to complete the circuit. As illustrated schematically in FIG. 6, the monitoring area 74 acts essentially as a resistor, as indicated by reference character R. When the monitoring area 74 is dry (e.g., before the presence of an insult), the resistance of the monitoring area is relatively high, for example, some resistance above 200 k$\Omega$. When the monitoring area 74 is wetted, for example by an insult, its resistance drops, for example, to some resistance less than 200 K$\Omega$ because of the electrically conductive nature of urine.

In another embodiment, the conductance of the monitoring area 74 of the pants 20 is measured. As stated above, urine is electrically conductive and the article 20, generally is not electrically conductive. Therefore, when the monitoring area 74 of the pants 20 is wetted, its conductance is greater than when it is dry. Other electrical properties of the pants 20, including impedance, may be measured without departing from the scope of this invention.

The measuring device 85 produces an analog output signal (FIG. 6) indicative of the electrical property of the monitoring area 74 of the pants 20. For example, the measuring device 85 can measure a voltage drop across the monitoring area 74, and produce an analog output signal corresponding to the voltage drop. The output voltage signal can be used to determine other electrical properties, such as resistance or current, by performing suitable calculations known in the art or using a reference table. For example, as is well known in the art, the voltage drop is indicative of the resistance of the pants when the current is constant. Thus, as explained below in further detail, the resistance of the pants 20 may be determined using the analog output signal of the measuring device 85.

In one embodiment of the present invention, a percent difference test is conducted on the measured resistance of the pants 20 to determine the presence (or lack thereof) of an insult in the pants as the pants are being worn by the wearer. In this embodiment, a proportional difference (e.g., a percent difference) in the measured electrical property of the monitoring area of the pants over time is determined, and this proportional difference is compared with a difference threshold value to determine if an insult is present in the pants.

Figure 7:
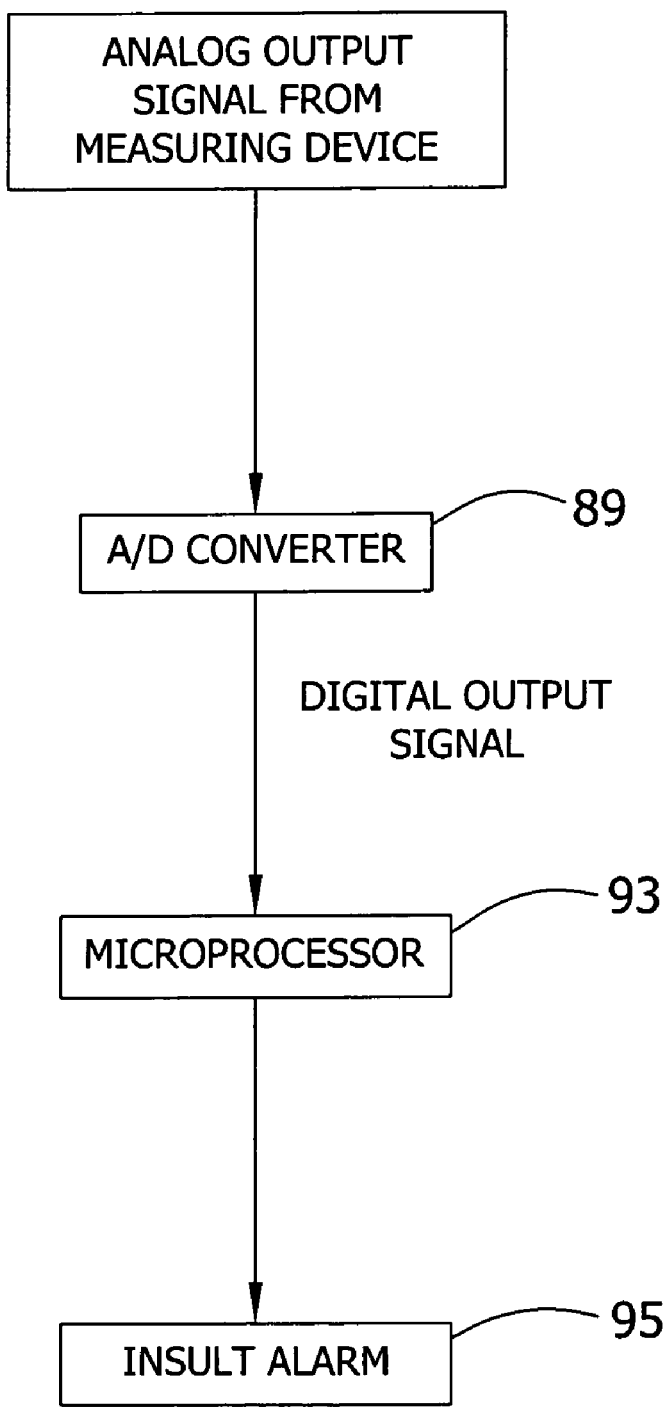
FIG. 7 is a block diagram for one embodiment of the invention illustrating an order of operation for components/devices of the invention, including a measuring device for measuring an electrical property of the pants and an analog-to-digital converter for converting an analog output from a measuring device into digital values to be read by a microprocessor.

In one example of this embodiment, illustrated in FIG. 7, an analog-to-digital converter 89 receives the analog output signal from the measuring device 85 and converts the signal into a digital output signal. A microprocessor 93 receives the digital output signal, which is representative of the magnitude of the electrical property (e.g., resistance) of the pants 20, and analyzes it to determine the presence of an insult. If the microprocessor 93 detects the presence of an insult, then it activates the insult alarm 95. The analog-to-digital converter 89 is a conventional device for converting analog signals into digital signal that can be read by a microprocessor. The analog-to-digital converter 89 of the present embodiment may be a separate device or it may be a component of the microprocessor 93. For illustrative purposes, the electrical property will hereinafter be referred to as resistance although, as noted above, it may be any variable property of the garment which reflects wetness.

Figure 8:
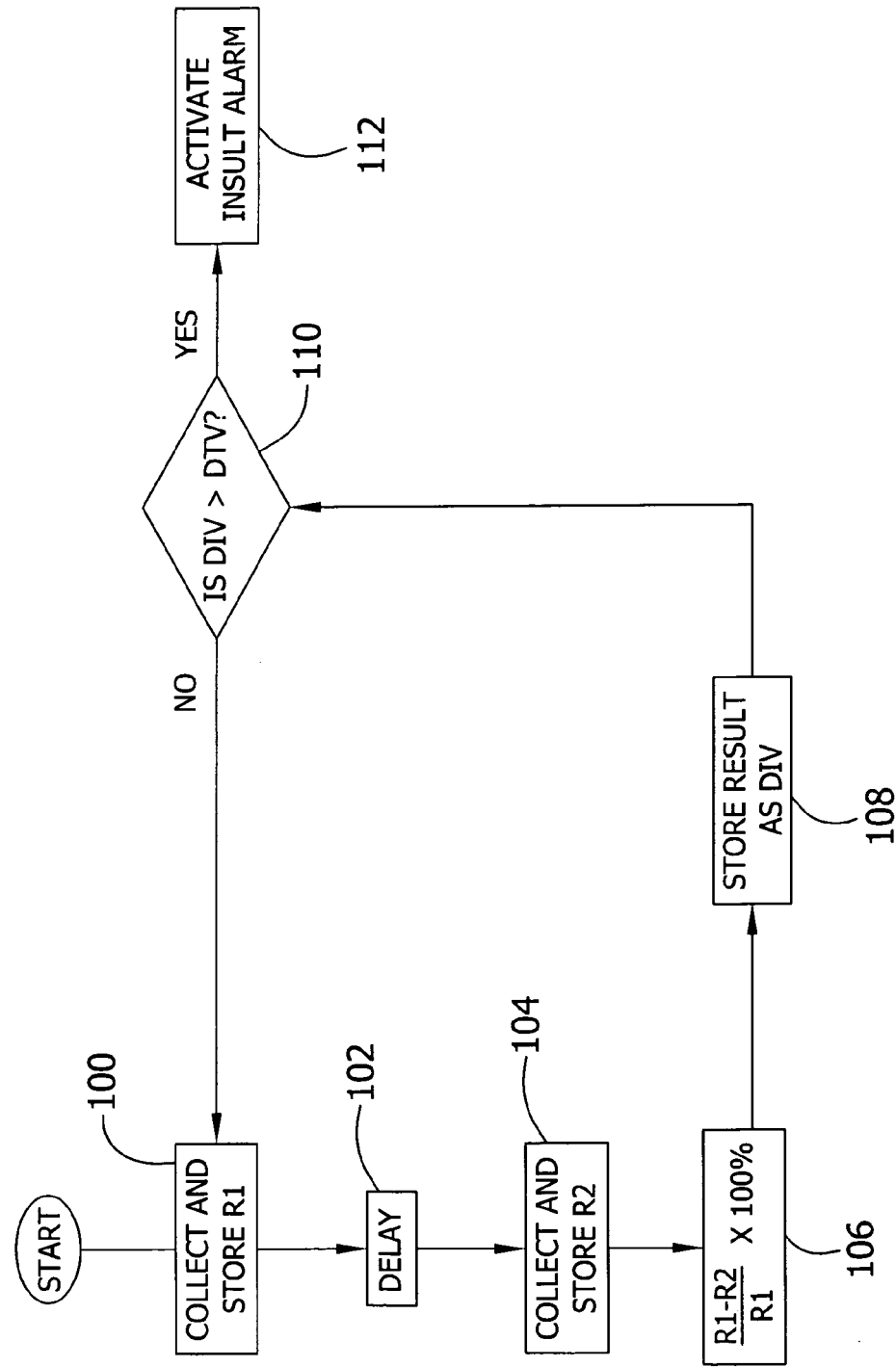
FIG. 8 is a block diagram of exemplary instructions for the microprocessor of the present invention for determining the presence of an insult using a proportional difference of the measured resistance of the pants.

FIG. 8 illustrates schematically the instructions of the microprocessor 93 for determining the percent difference in the resistance of the pants 20 and comparing the percent difference to a difference threshold value to determine the presence of an insult. At instruction 100 the microprocessor 93 collects and stores in its memory a first resistance value (R1) from the digital output signal. The microprocessor 93 then delays sampling for a period of time at instruction 102 before collecting and storing a second resistance value (R2) at instruction 104. The delay may be programmed or may be a function of the sampling rate of the A/D converter 89 and/or the microprocessor 93.

With the stored first and second resistance values (R1, R2), at instruction 106 the microprocessor 93 subtracts the second value (R2) from the first value (R1) and divides the resulting difference by the first value (R1) and multiplies the resulting quotient by 100%. The resulting value is stored as a difference indicator value (DIV) at instruction 108.

At instruction 110, the resulting difference indicator value (DIV) is then compared to a difference threshold value (DTV) to determine if an insult is present. For example, if the difference indicator value (DIV) is greater than the difference threshold value (DTV) then this is indicative of the presence of an insult. As an example, the difference threshold value (DTV) may be a value between 10% and 20% (indicating a 10% and 20% decrease in resistance), or more particularly, the difference threshold value may be about 15%. If the comparison of the difference indicator value to the difference threshold value is indicative of the presence of an insult, then, if there are no other indicators, the microprocessor 93 activates the insult alarm 95 at instruction 112 to inform the caregiver and/or the wearer of the presence of an insult. If, however, the comparison of the difference indicator value (DIV) to the difference threshold value (DTV) is not indicative of the presence of an insult, then, if there are no other indicators, the microprocessor 93 is instructed to repeat the above steps for determining new difference indicator values and comparing them to the difference threshold value until an insult is indicated.

The percent difference test is meant to be more accurate (that is, detects insults better and detects false-positives less frequently) than the conventional magnitude threshold test because the percent difference test is independent of the magnitude of the resistance of the pants prior to an insult. The percent difference test focuses on the amount of change in the resistance and allows for more accurate detection of multiple voids.

As an example, if the resistance changes from 200 K$\Omega$ to 50 K$\Omega$, giving a difference indicator value of 75%, and the difference threshold is 20%, then the insult alarm would be activated. As another example, if the resistance changes from 60 K$\Omega$ to 50 K$\Omega$, giving a difference indicator value of 17%, and the difference threshold is 20%, then the insult alarm would not be activated.

In another example of the difference embodiment, the instructions for the microprocessor 93 may involve determining the percent difference between previous successive resistance values compared to a present value, e.g., the difference between a third resistance value (R3) and second resistance value (R2) and the third value (R3) and a first resistance value (R1).

Figure 9:
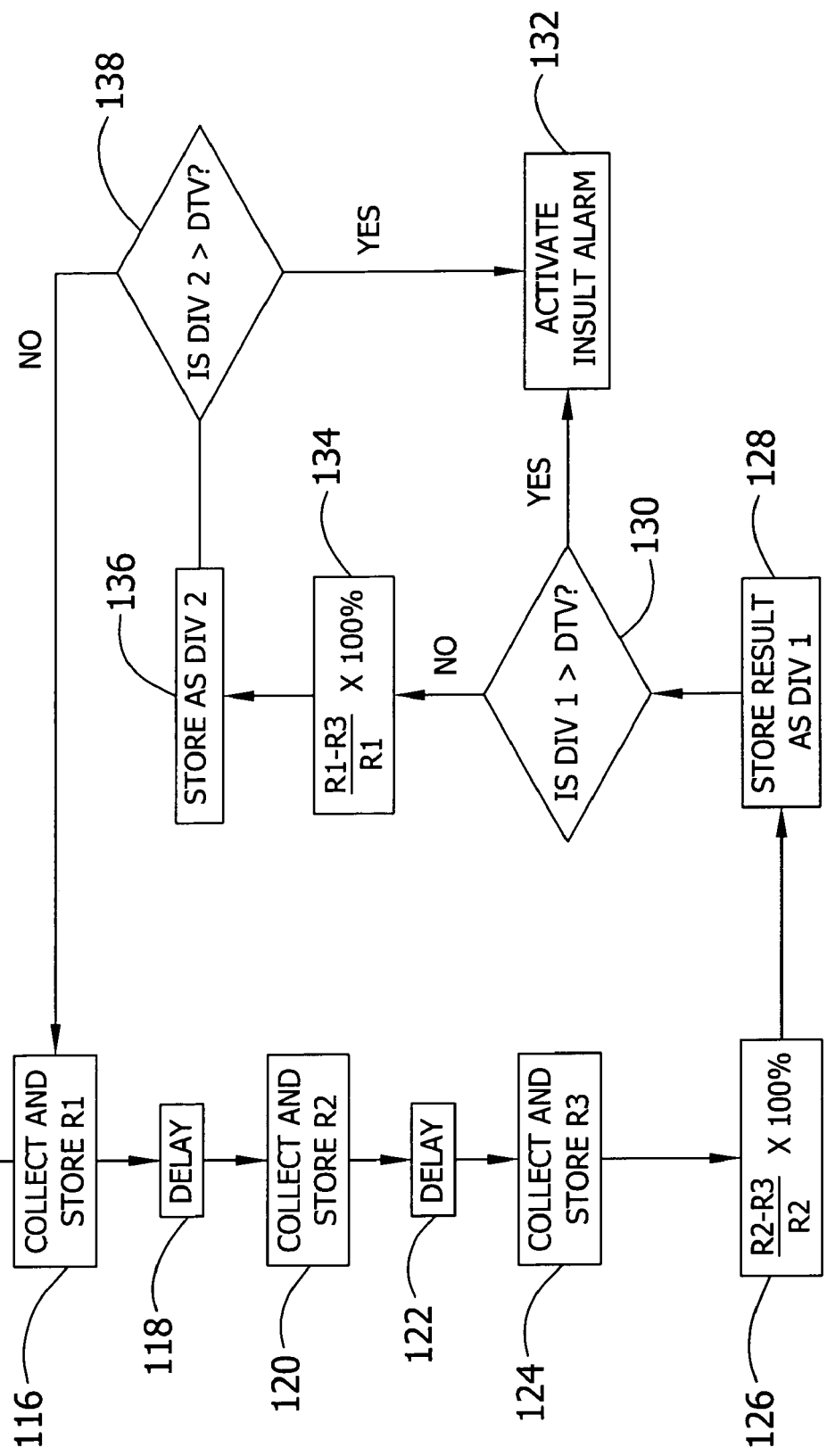
FIG. 9 is a block diagram of exemplary instructions for the microprocessor of the present invention for determining the proportional difference of the measured resistance of the pants using successive resistance values.

FIG. 9 illustrates schematically the instructions of the microprocessor for this embodiment. At instruction 116 the microprocessor 93 collects and stores in its memory a first resistance value (R1) from the digital output signal at a first time. The microprocessor then delays for a period of time at instruction 118 before collecting and storing a second resistance value (R2) at instruction 120. At instruction 122 the microprocessor 93 delays, and then it collects and stores a third resistance value (R3) at instruction 124. With the values stored, the microprocessor 93 subtracts the second value (R2) from the third value (R3) and divides the resulting difference by the second value (R2) at instruction 126 to get a percent difference. The percent difference is stored as a first difference indicator value (DIV 1) at instruction 128 and compared to the difference threshold value (DTV) at instruction 130 to determine if the comparison is indicative of the presence of an insult.

If the comparison of the first difference indicator value (DIV 1) is indicative of the presence of an insult, then the insult alarm 95 is activated at instruction 132. If the comparison is not indicative of the presence of an insult then the microprocessor is instructed at 134 to calculate a second difference indicator value (DIV 2) by subtracting the first value (R1) from the third value (R3) and dividing the difference by the first value (R1). This second percent difference (DIV 2) is stored as the second difference indicator value (DIV 2) at instruction 136. At instruction 138 the second difference indicator value (DIV 2) is then compared to the difference threshold value (DTV).

If the comparison of the second difference indicator value (DIV 2) to the difference threshold value (DTV) is indicative of the presence of an insult, then the insult alarm is activated at the instruction 132. If the comparison is not indicative of the presence of an insult, then the microprocessor is instructed to repeat the above steps for comparing a new difference indicator value to the difference threshold value until an insult is indicated.

In the above example, if either the first indicator value (DIV 1) or the second indicator value (DIV 2) is below the difference threshold value (DIV), the microprocessor 93 activates the insult alarm 95. It is also contemplated that only when both the first indicator value and the second indicator value are greater than the threshold value (i.e., both comparisons are indicative of the present of an insult) would the alarm 95 be indicated. For example, if the first, second, and third values are 85 KΩ, 75 KΩ, and 65 KΩ, respectively, then the difference indicator values for R3-R2 and R3-R1 are 31% and 24%, respectively. Assuming the difference threshold value is 20%, the insult alarm would not be activated when comparing R3-R2 to threshold value, but would be activated when comparing R3-R1 to threshold value.

In another embodiment of the present invention, a rate of change test is conducted on the measured electrical property of the pants 20 to determine the presence (or lack thereof) of an insult. In this embodiment, a rate of change of the measured electrical property of the monitoring area 74 of the pants 20 over a period of time is determined, and this rate of change is compared with a rate threshold value to determine if an insult is present in the pants.

Figure 10:
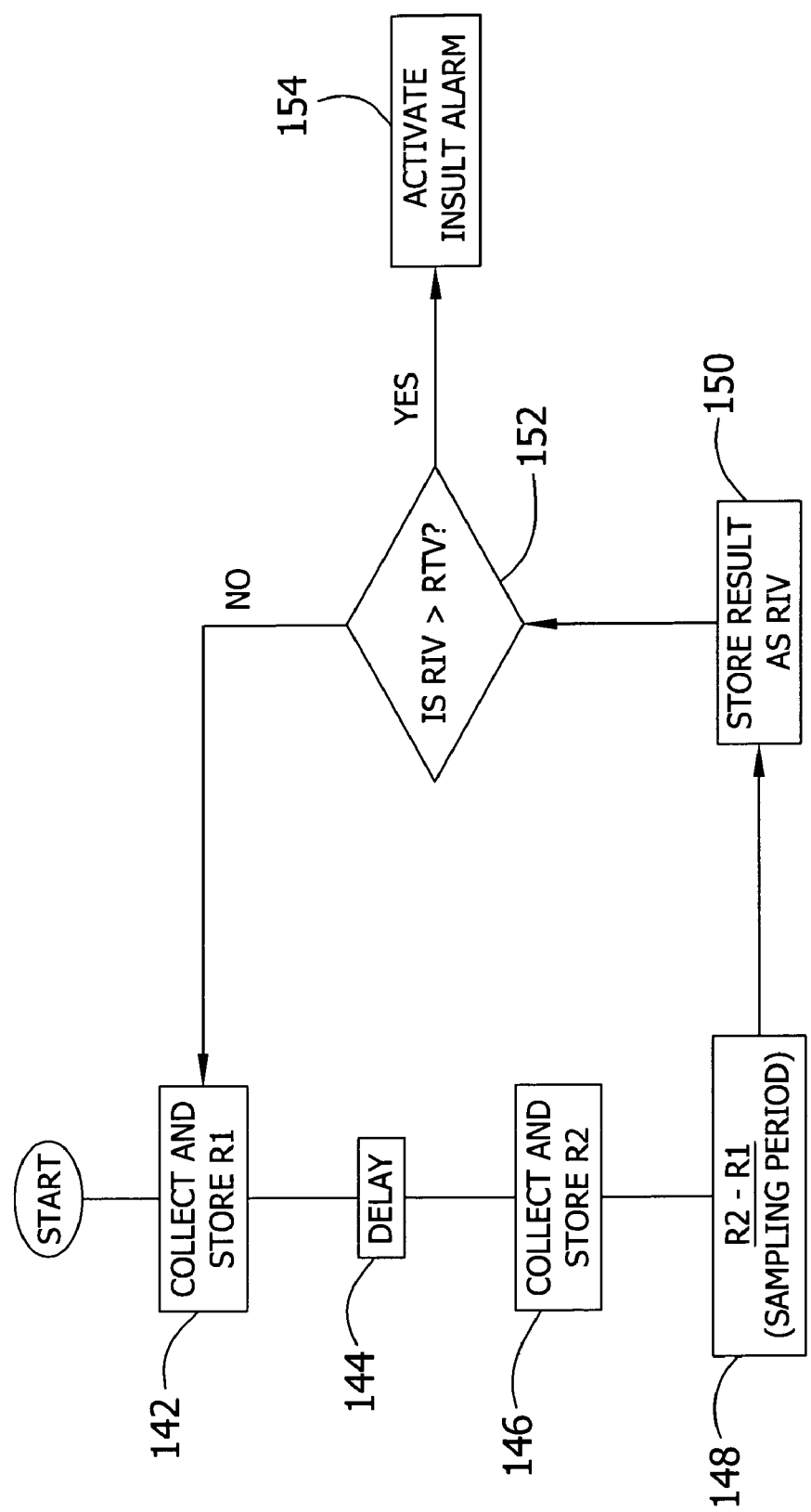
FIG. 10 is a block diagram of exemplary instructions for the microprocessor of the present invention for determining the presence of an insult using a rate of change of the measured resistance of the pants.

In one example of this embodiment, the output signal from the measuring device is converted to a digital output signal (via the analog-to-digital converter 89, for example) and received by the microprocessor 93 as explained above and shown in FIG. 7. FIG. 10 illustrates schematically one example of the instructions of the microprocessor 93 for determining the rate of change in the resistance of the pants 20 and comparing the rate of change to a rate threshold value to determine the presence of an insult. At instruction 142 the microprocessor 93 collects and stores in its memory a first resistance value (R1) from the digital output signal at a first time. The microprocessor 93 then delays for a period of time at instruction 144 before collecting and storing a second resistance value (R2) at instruction 146. As explained above, the delay is determined by the sampling period of the A/D converter 89 and/or is programmable by instructions within the microprocessor 93.

With the stored first and second values (R1, R2), the microprocessor 93 subtracts the second value from the first value and divides the resulting difference by the sampling period at instruction 148. The resulting value is stored as a rate indicator value (RIV) at instruction 150. At instruction 152, the microprocessor 93 compares the resulting rate indicator value (RIV) to a rate threshold value (RTV) to determine if an insult is present. For example, if the rate indicator value (RIV) is greater than the rate threshold value (RTV) then this is indicative of the presence of an insult. If the comparison of the rate indicator value to the rate threshold value is indicative of the presence of an insult, then, if there are no other indicators, the microprocessor 93 activates the insult alarm 95 to inform the caregiver and/or the wearer of the presence of an insult at instruction 154. If, however, the comparison of the rate indicator value to the rate threshold value is not indicative of the presence of an insult, then, if there are no other indicators, the microprocessor 93 is instructed to repeat the above steps for determining new rate indicator values and comparing them to the rate threshold value until an insult is indicated.

Like the percent difference test discussed above, the rate of change test is meant to be more accurate (that is, detects insults better and detects false-positives less frequently) than the conventional magnitude threshold test because the rate of change test is independent of the magnitude of the electrical property of the pants and focuses on how quickly the property changes.

For example, if the resistance changes from 200 KΩ to 50 k over a period of 0.3 seconds, giving a rate indicator value of 450 KΩ/s, and the rate threshold value is 25 KΩ/s, then the insult alarm would be activated. As another example, if the resistance changes from 75 KΩ to 68 KΩ over a period of 0.3 seconds, giving a rate indicator value of 21 KΩ/s, and the rate threshold value is 25 KΩ/s, then the insult alarm would be not activated. The drop in resistance of this latter example may be caused by variations within saturated pants, the presence of sweat, or a number of other causations other than an insult.

Figure 11:
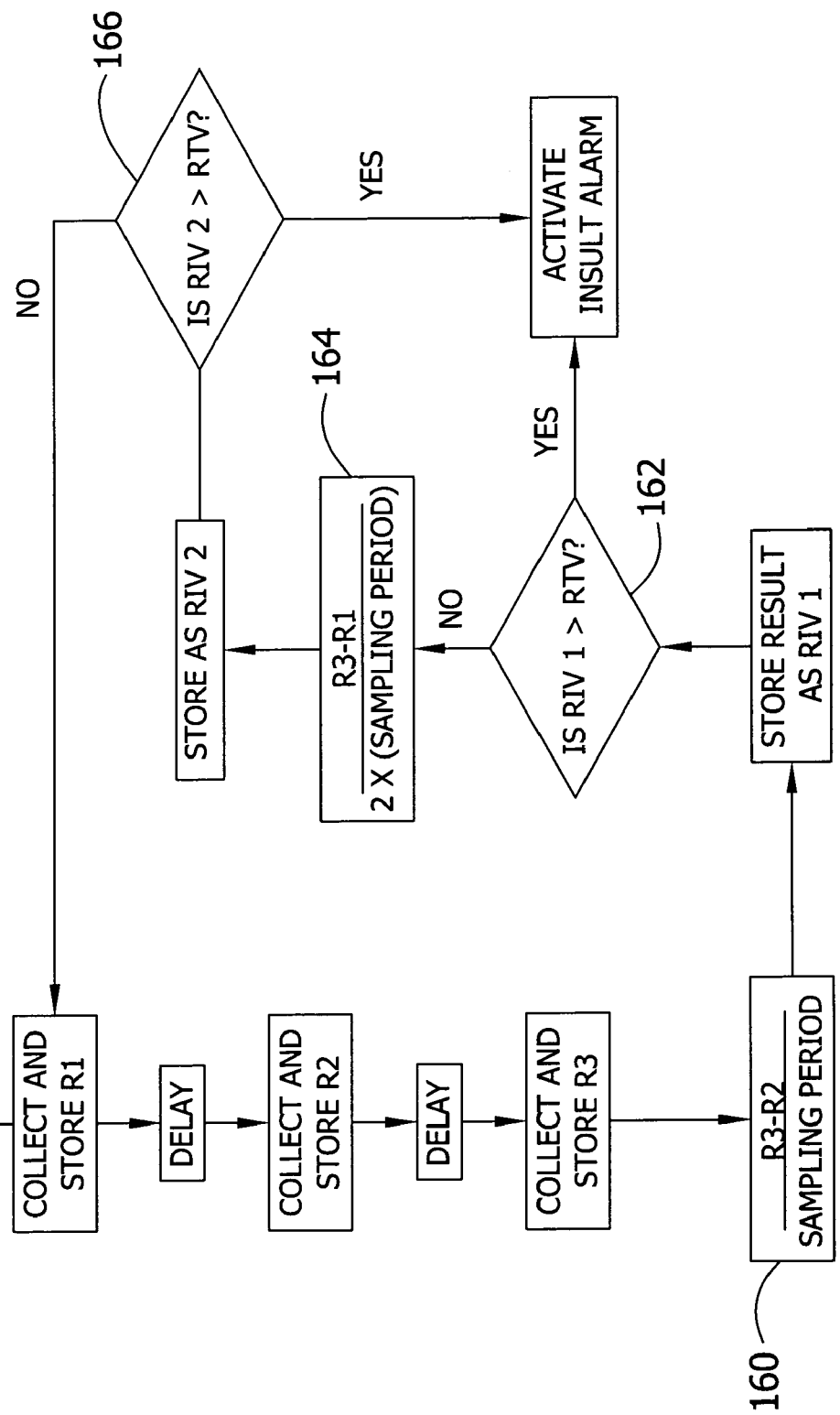
FIG. 11 is a block diagram of exemplary instructions for the microprocessor of the present invention for determining the rate of change of the measured resistance of the pants using successive resistance values.

As illustrated in FIG. 11, in another example of the rate of change embodiment, the instructions for the microprocessor may involve determining the rate of change between previous successive values compared to a present value (e.g., the rate of change between a third value and second value and a third value and first value). This example is substantially similar to the instruction given in FIG. 9 with respect to the percent difference embodiment, except that the first rate indicator value (RIV 1) between third value (R3) and the second value (R2) is determined at instruction 160 and compared to the rate threshold value (RTV) at instruction 162, and the second rate indicator value (RIV 2) between third value (R3) and the first value (R1) is determined at instruction 164 and compared to the rate threshold value (RTV) at instruction 166.

Figure 12:
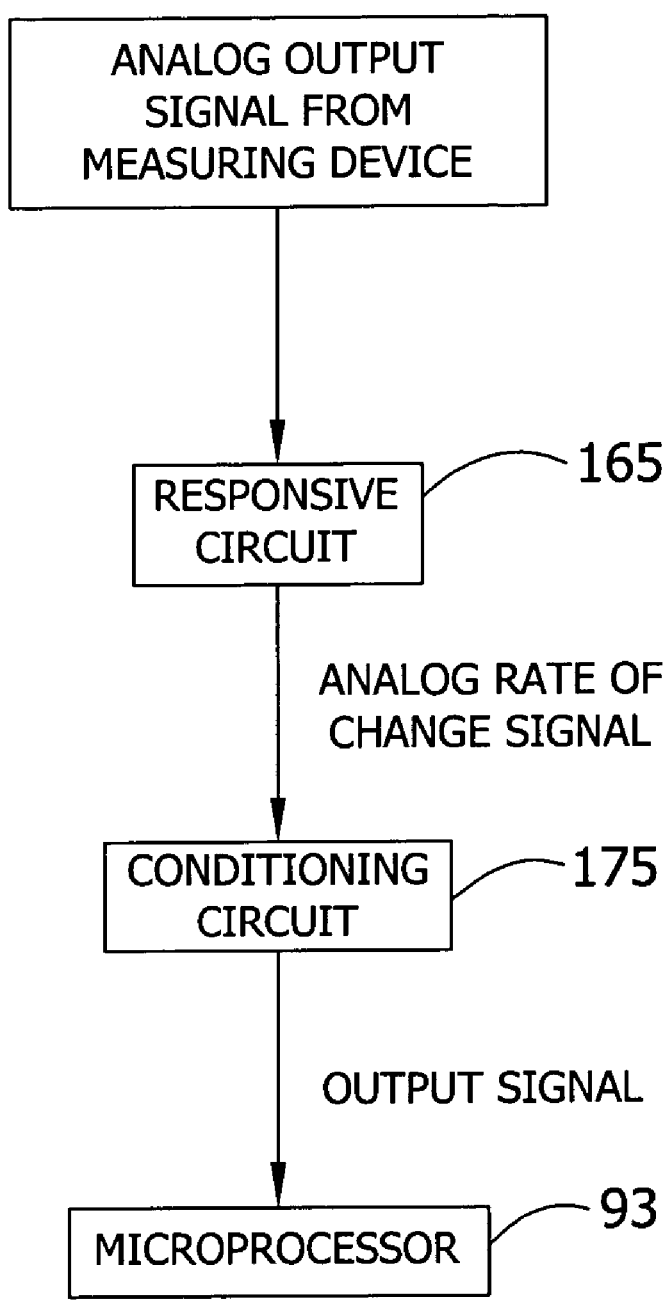
FIG. 12 is a block diagram of devices/components of one embodiment of the present invention for determining the rate of change of the resistance of the pants, including a responsive circuit and a conditioning circuit.

In another example of the rate of change embodiment (FIGS. 12 and 13) the output signal from the measuring device 85 is fed through a responsive circuit 165 that produces an analog rate of change signal indicative of the rate of change of the analog output signal from the measuring device. For example, when the measuring device 85 generates a voltage signal, an operational amplifier, such as a differentiator, may be used to generate a signal indicative of the rate of change of the voltage. An exemplary differentiator suitable for use with this embodiment of the invention is illustrated schematically in FIG. 14. The input 169 of the differentiator 167 of FIG. 14 is the analog output signal from the measuring device 85, and the output 170 of the differentiator is a linear representation of the change in the rate of change of the resistance profile.

Referring back to FIG. 12, in one example using the responsive circuit 165 of the present embodiment, a conditioning circuit 175 receives the analog right of change signal from the responsive circuit 165 . The conditioning circuit 175 is a threshold detector determining whether the analog rate of change signal has a value greater than a value which corresponds to the rate threshold value. The conditioning circuit 175 produces a positive output voltage (e.g., +5 volts) if the output signal from the responsive circuit 165 indicates a rate of change that is greater than the rate threshold value. Otherwise, the conditioning circuit 175 produces a different signal such as no signal (e.g., 0 volts) or a negative signal. In response to the output from the conditioning circuit 175, the microprocessor 93 recognizes the positive signal as corresponding to the insult and activates the insult alarm 95 whereas the microprocessor ignores the no signal or negative signal. Alternatively, the microprocessor can be programmed to respond to no signal (e.g., 0 volts) or a negative signal (e.g., −5 volts) to activate the insult alarm 95.

Figure 13:
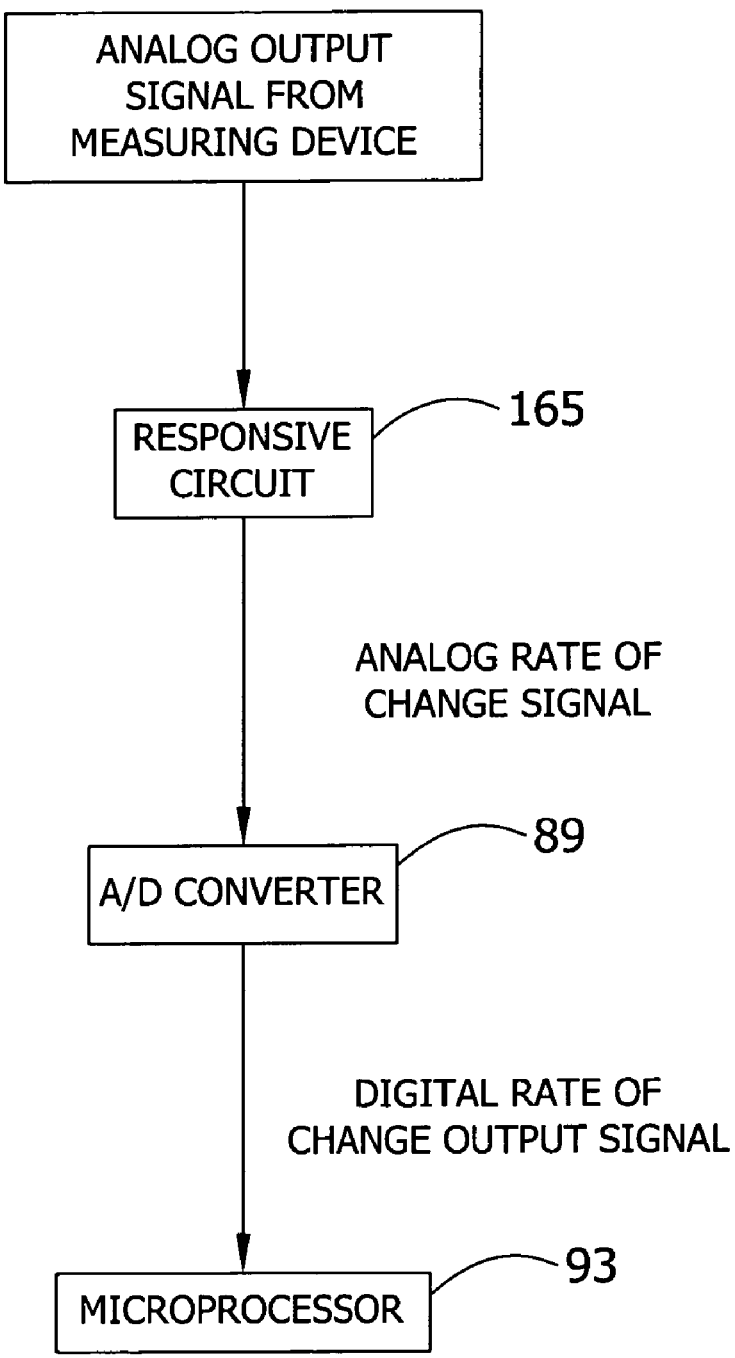
FIG. 13 is a block diagram of devices/components of another embodiment the present invention for determining the rate of change of the resistance of the pants, including a responsive circuit and an analog-to-digital converter.
Figure 14:
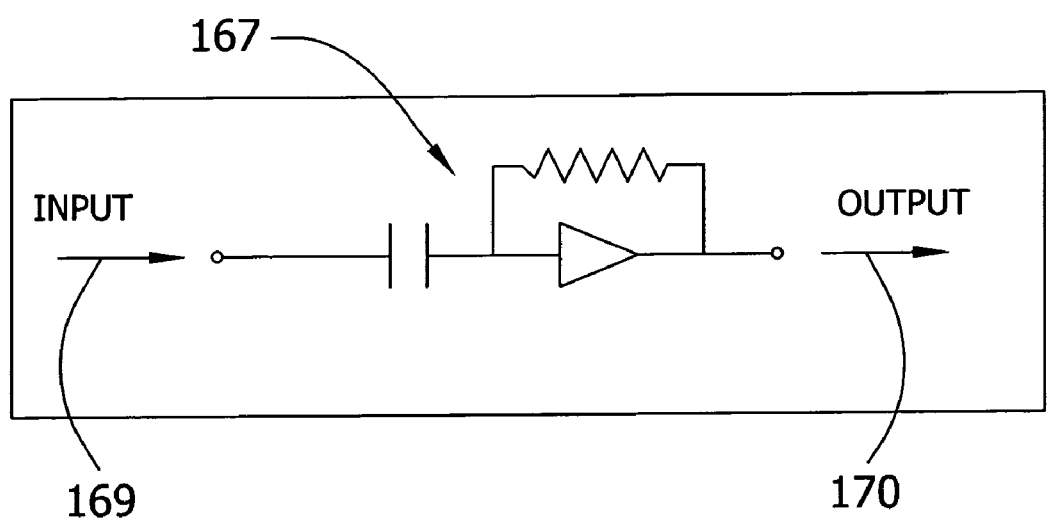
FIG. 14 is a schematic of an exemplary responsive circuit in the form of a differentiator.

Referring to FIG. 13, alternatively, in another example using the responsive circuit 165, an analog-to-digital converter 89 converts the analog rate of change signal from the responsive circuit into a digital output signal indicative of the rate of change of the resistance of the pants. The microprocessor 93 receives the digital output signal to collect and store rate indicator values. The stored digital values are indicative of rate indicator values, and the microprocessor 93 compares the stored values to the rate threshold value to determine if there is an indication of the presence of an insult in the pants.

In another embodiment, both the percent difference embodiment and the rate of change embodiment may be combined into a single embodiment, whereby the insult alarm 95 is activated only if both the comparison of the difference indicator value (DIV) to the difference threshold value (DTV) and the comparison of the rate indicator value (RIV) to the rate threshold value (RTV) are indicative of the presence of an insult. Alternatively, the insult alarm may be activated if either the comparison of the difference indicator value to the difference threshold value or the comparison of the rate indicator value to the rate threshold value are indicative of the presence of an insult.

One example of this embodiment (not shown) is a combination of the examples of FIGS. 8 and 10 (using R2–R1) or FIGS. 9 and 11 (using R3–R2 and R3–R1) where the analog output signal from the measuring device is converted to a digital output signal and the microprocessor is instructed to compute both the rate indicator values and the difference indicator values and compare both values to respective threshold values to determine the presence of an insult using the digital output signal.

Figure 15:
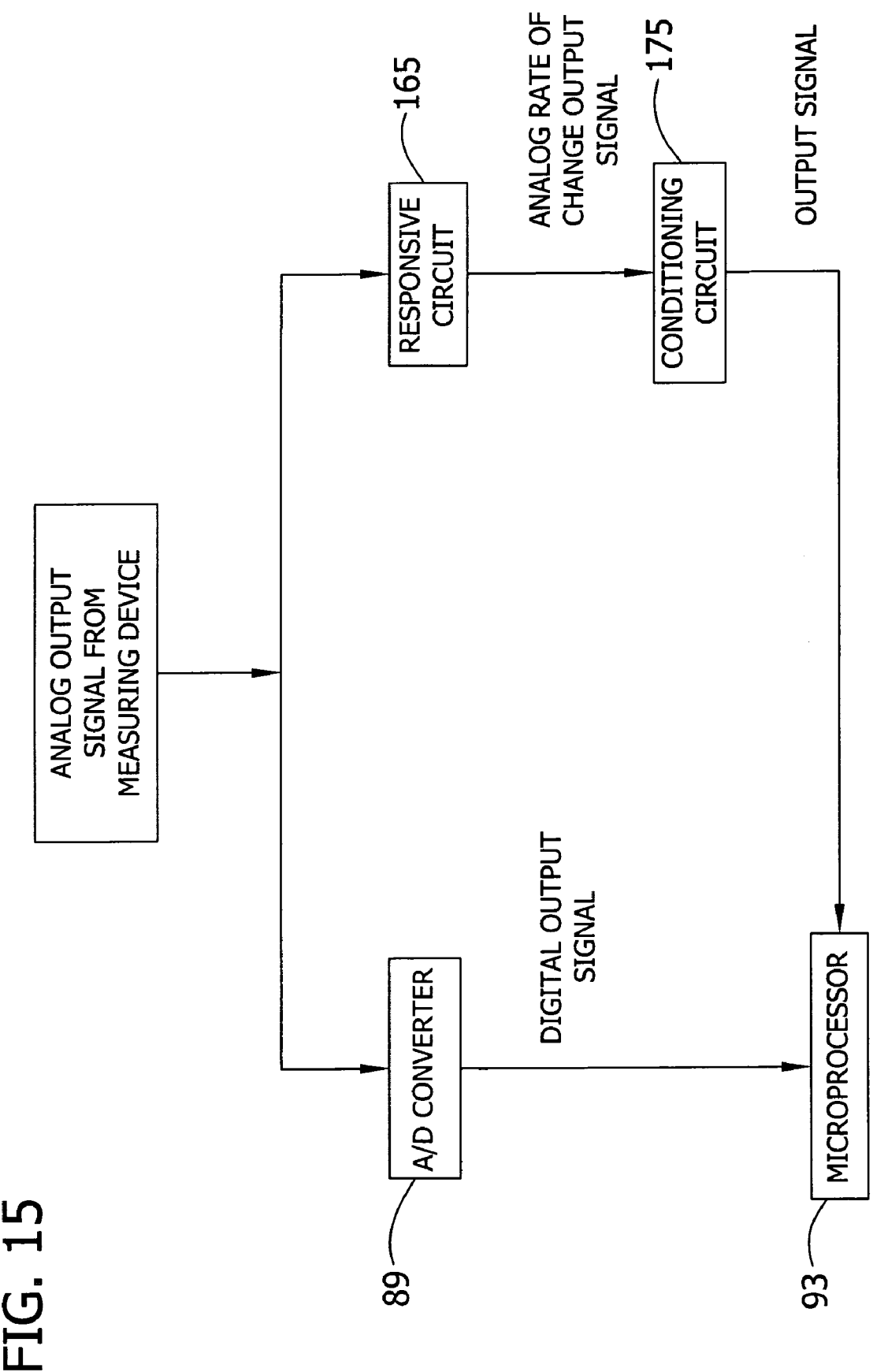
FIG. 15 is block diagram of an embodiment of the present invention combining the embodiments illustrated in FIGS. 7 and 12 to determine the presence of an insult in the pants using a proportional difference and a rate of change in the resistance of the pants.

Another example is illustrated in FIG. 15. This example is a combination of aspects of the embodiments of FIGS. 7 and 12. The analog output signal from the measuring device 85 is provided to both an analog-to-digital converter 89 and a responsive circuit 165. The microprocessor 93 uses the digital output signal from the analog-to-digital converter 89 to compute the difference indicator value (and optionally a second difference indicator value) and determine if the comparison of the indicator value(s) to the difference threshold value is indicative of the presence of an insult, as illustrated in FIGS. 8 and 9. As explained above and illustrated in FIG. 12, the conditioning circuit 175 receives the analog rate of change signal from the responsive circuit 165 and produces a corresponding output signal to the microprocessor 93 indicative of the presence of an insult. As explained above, the microprocessor 93 may be instructed to activate the insult alarm 95 if both the percent difference test and the rate of change test indicates an insult, or alternatively, the microprocessor may be instructed to activate the insult alarm if either the percent difference test or the rate of change test indicates an insult.

Figure 16:
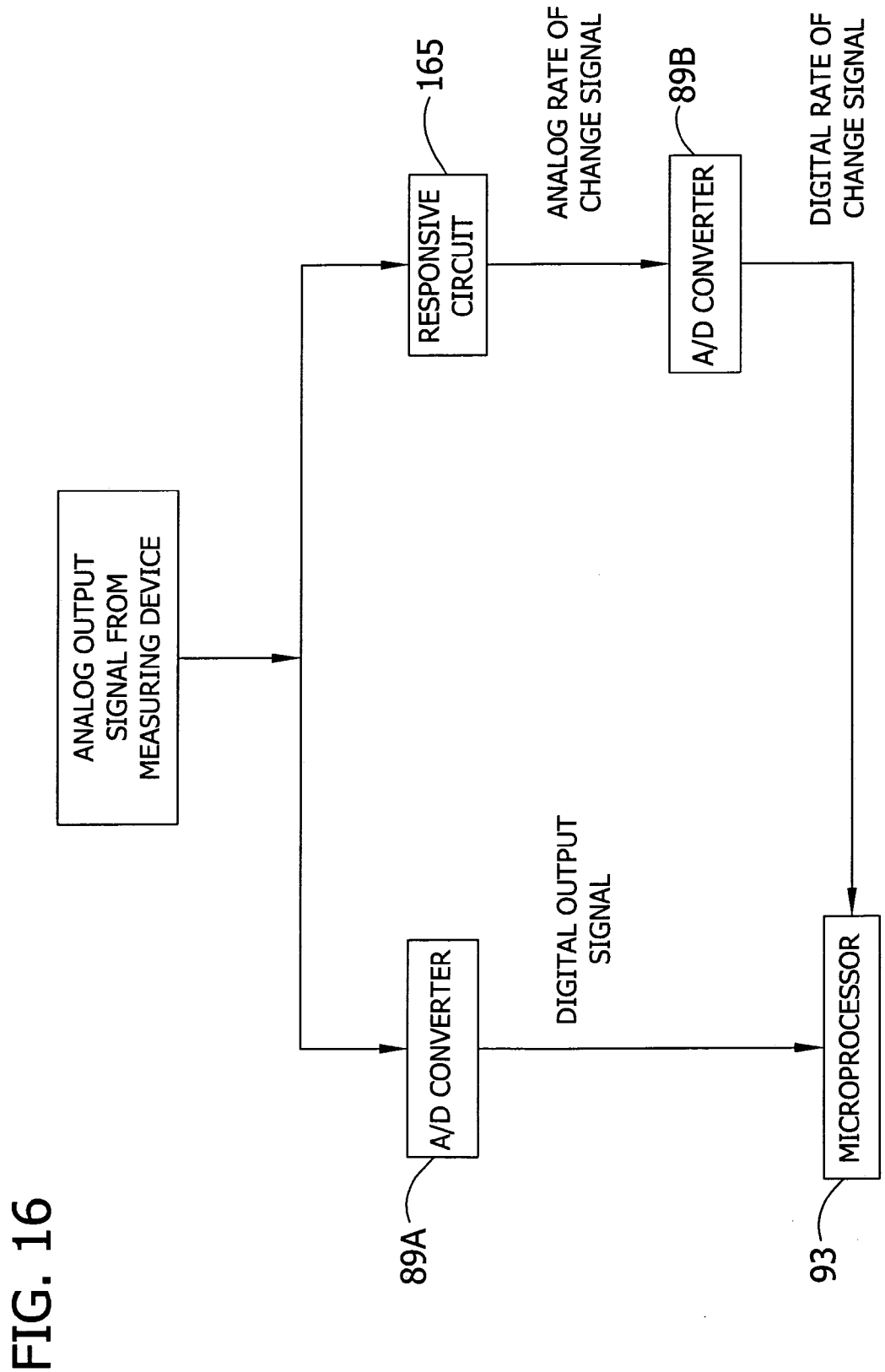
FIG. 16 is a block diagram of another embodiment of the present invention combining the embodiments illustrated in FIGS. 7 and 13 to determine the presence of an insult in the pants using a proportional difference and a rate of change in the resistance of the pants.

Yet another example of the present embodiment is illustrated in FIG. 16. This example is a combination of the aspects of the embodiments of FIGS. 7 and 13. The analog output signal from the measuring device 85 is provided to both a first analog-to-digital converter 89A and a responsive circuit 165. The microprocessor 93 uses the digital output signal from the first analog-to-digital converter 89A to compute the difference indicator value (an optionally a second difference indicator value) and determine if the comparison of the value(s) to the difference threshold value is indicative of the presence of an insult, as illustrated in FIGS. 8 and 9. As illustrated in FIG. 13, the analog rate of change signal from the responsive circuit 165 is converted into a digital rate of change signal by a second analog-to-digital converter 89B. The digital rate of change signal is then sent to the microprocessor 93, where the microprocessor compares the digital values to a rate threshold value to indicate the presence of an insult. Again, depending on the instruction of the microprocessor 93, either the insult alarm 95 is activated when either both the rate of change test and the percent difference test indicates an insult or when either test indicates an insult.

In another embodiment of the present invention (FIGS. 17 and 18), a false-positive check is implemented to determine if a measured electrical property is either too high or too low to have been caused by the presence of an insult. For example, if the resistance of the pants 20 is very high (e.g., above 5,000 KΩ) then this is may be an indication that the sensor has not been properly insulated. As another example, if the resistance of the pants is very low (e.g., below 0.5 KΩ) then this is may be an indication that the conductors inside the pants are touching, for example, thereby forming a short circuit. This false-positive check embodiment may be used in combination with any other embodiment of this invention or with any other embodiment for determining the presence of an insult. For example, this embodiment may be used to check if the determined rate of change and/or the determined percent difference are either too high or too low to be true indications of the presence of an insult.

Figure 17:
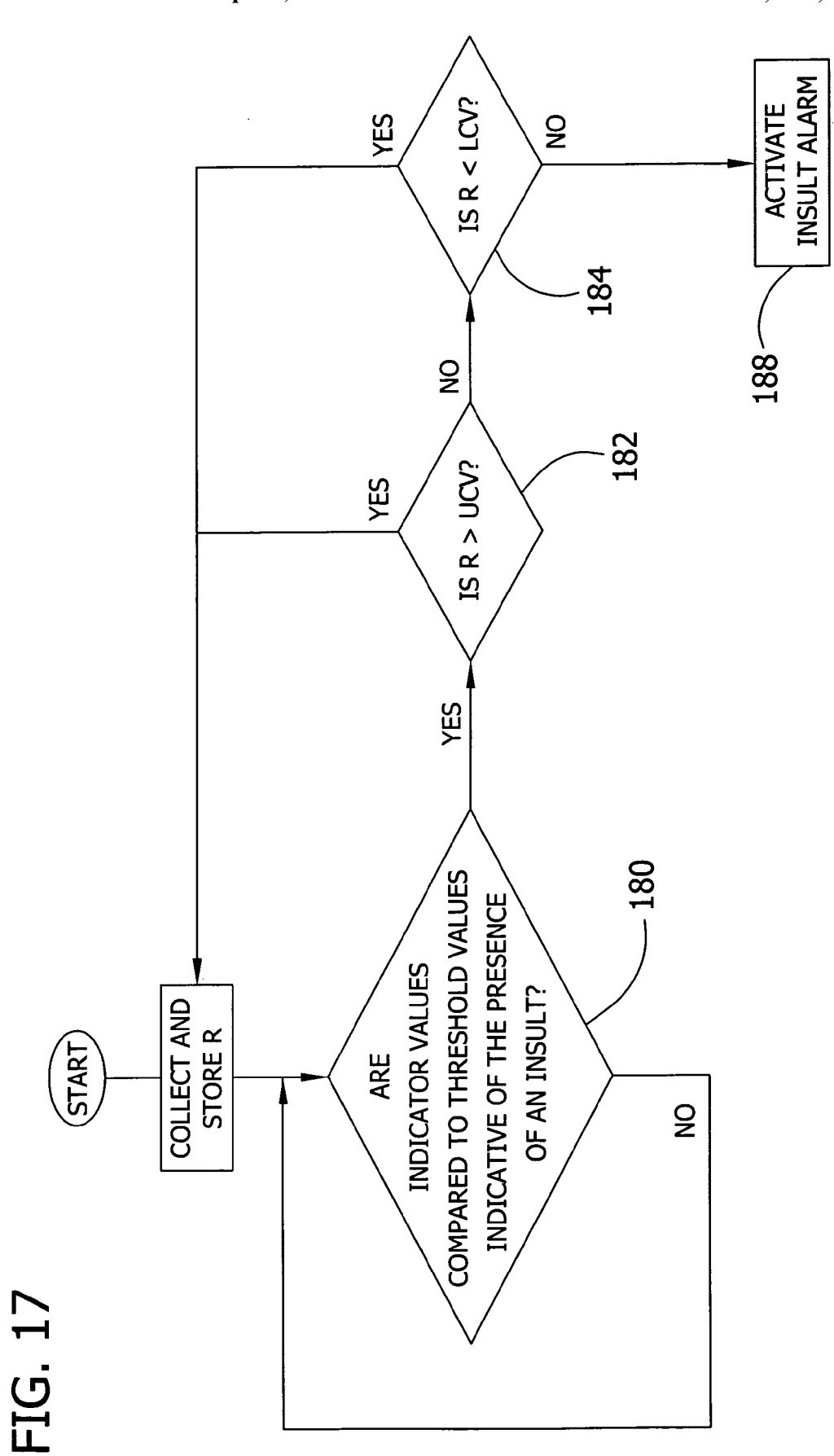
FIG. 17 is a block diagram of instructions for the microprocessor for determining whether a measured resistance is either too high or too low to be an accurate indication of the presence of an insult.
Figure 18:
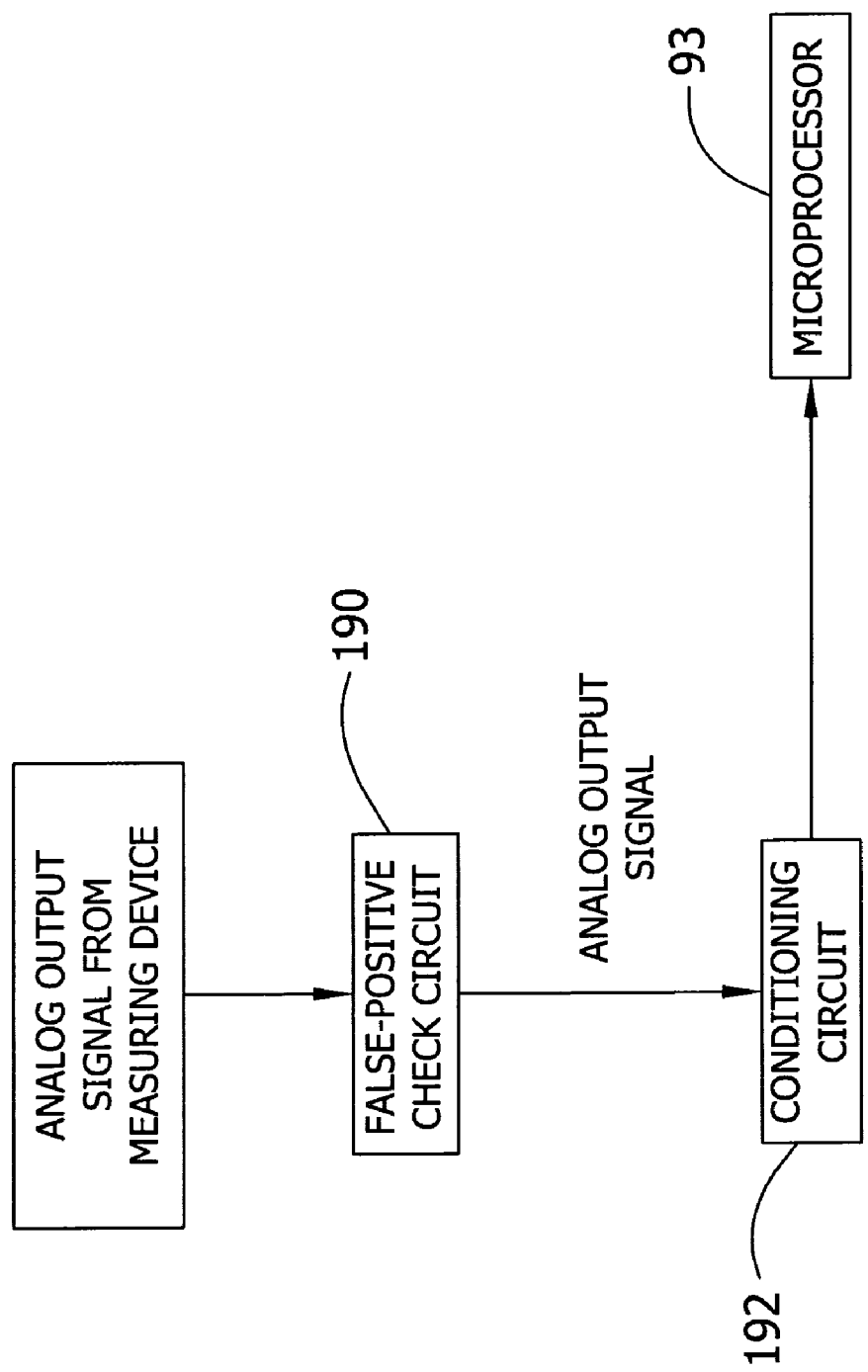
FIG. 18 is a block diagram of the devices/components of another embodiment of the present invention for determining whether a measured resistance is either too high or too low to be an accurate indication of the presence of an insult, including a false-positive check circuit.

In one example, illustrated schematically in FIG. 17, after the microprocessor 93 determines that the comparison of an indicator value (e.g., difference indicator value, rate indicator value, or magnitude indicator value) to a respective threshold value is indicative of the presence of an insult (indicated by reference numeral 180, the microprocessor, at instructions 182 and 184, respectively, is instructed to determine whether the present resistance value (R) is greater than an upper check value (UCV) or less than a lower check value (LCV). If the present resistance value (R) is either greater than the upper check value (UCV) or less than the lower check value (LCV), then the microprocessor 93 is instructed to repeat the previous operations using a new resistance value, when applicable. If the present resistance value is neither greater than the upper check value nor less than the lower check value, then the microprocessor 93 is instructed at instruction 188 to activate the insult alarm 95, if no other intervening steps are present.

In another example of this embodiment (FIG. 18), a false-positive check circuit 190 is used to determine whether a resistance value is above or below the upper and lower check values, respectively. As illustrated schematically in FIG. 18, the analog output signal from the measuring device 85 is sent to the false-positive check circuit 190. The analog output signal of the check circuit 190 is indicative of whether the present resistance value is above or below the upper and lower check values, respectively. In the particular example of FIG. 18, a conditioning circuit 192 receives the analog output signal of the check circuit 190 and produces an output signal to the microprocessor 93 indicative of the resistance value being above or below the upper and lower check values, respectively. Alternatively, in another example (not shown), the analog output signal of the check circuit can be converted into a digital output signal using an analog-to-digital converter. In this example, the microprocessor receives the digital output signal from the converter and compares the digital values to the upper and lower check values to determine if there is a false positive.

Figure 19:
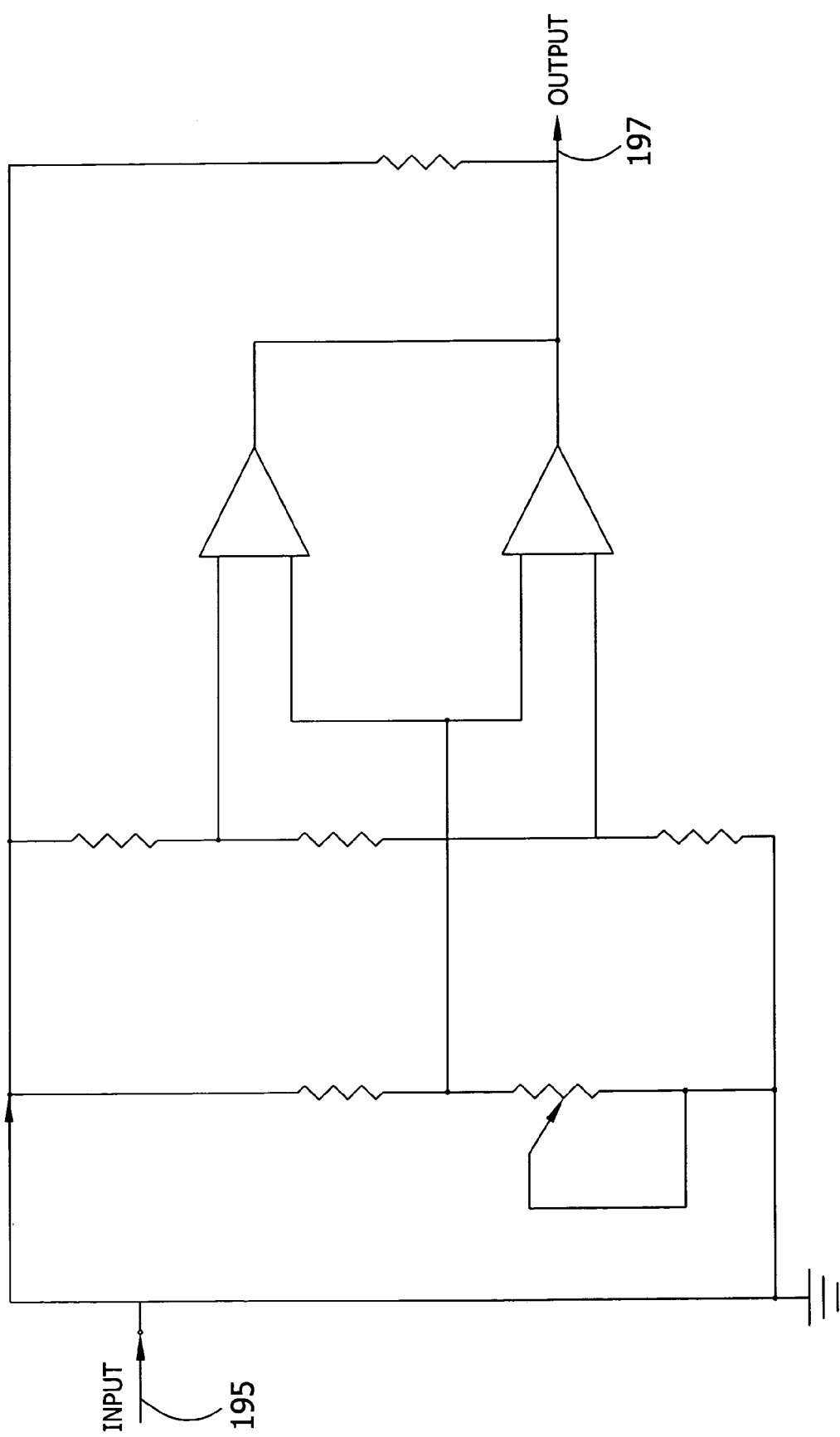
FIG. 19 is a schematic of an exemplary false-positive check circuit.

As an example, the check circuit 190 may comprise a window comparator circuit, as illustrated in FIG. 19. The check circuit 190 may comprise other types of circuits without departing from the scope of this invention. The input 195 of the check circuit 190 is the analog output signal from the measuring device 85, and the output 197 of the circuit is indicative of whether the resistance is above or below the upper and lower check values, respectively.

In another embodiment of the present invention, the microprocessor 93 is instructed to determine when the pants 20 are saturated. Typically, when the pants 20 are saturated, by urine for example, a microprocessor may continue to indicate the presence of an insult (e.g., continue to activate the insult alarm) even though the wearer has not produced another insult. This false-positive is typical when the test or indicator for the presence of an insult is comparing the resistance (or other electrical property) of the pants to a magnitude threshold value, as it typical in conventional monitoring systems. The false-positive occurs because the resistance of saturated pants, for example, is typically continuously less then the magnitude threshold value. Thus, according to this embodiment, the monitoring system of the present invention informs the caregiver and/or the wearer that the pants are saturated and that the pants should be changed and the monitoring system (or at least the components of the system within the housing) should be placed on a new pair of dry pants.

Figure 20:
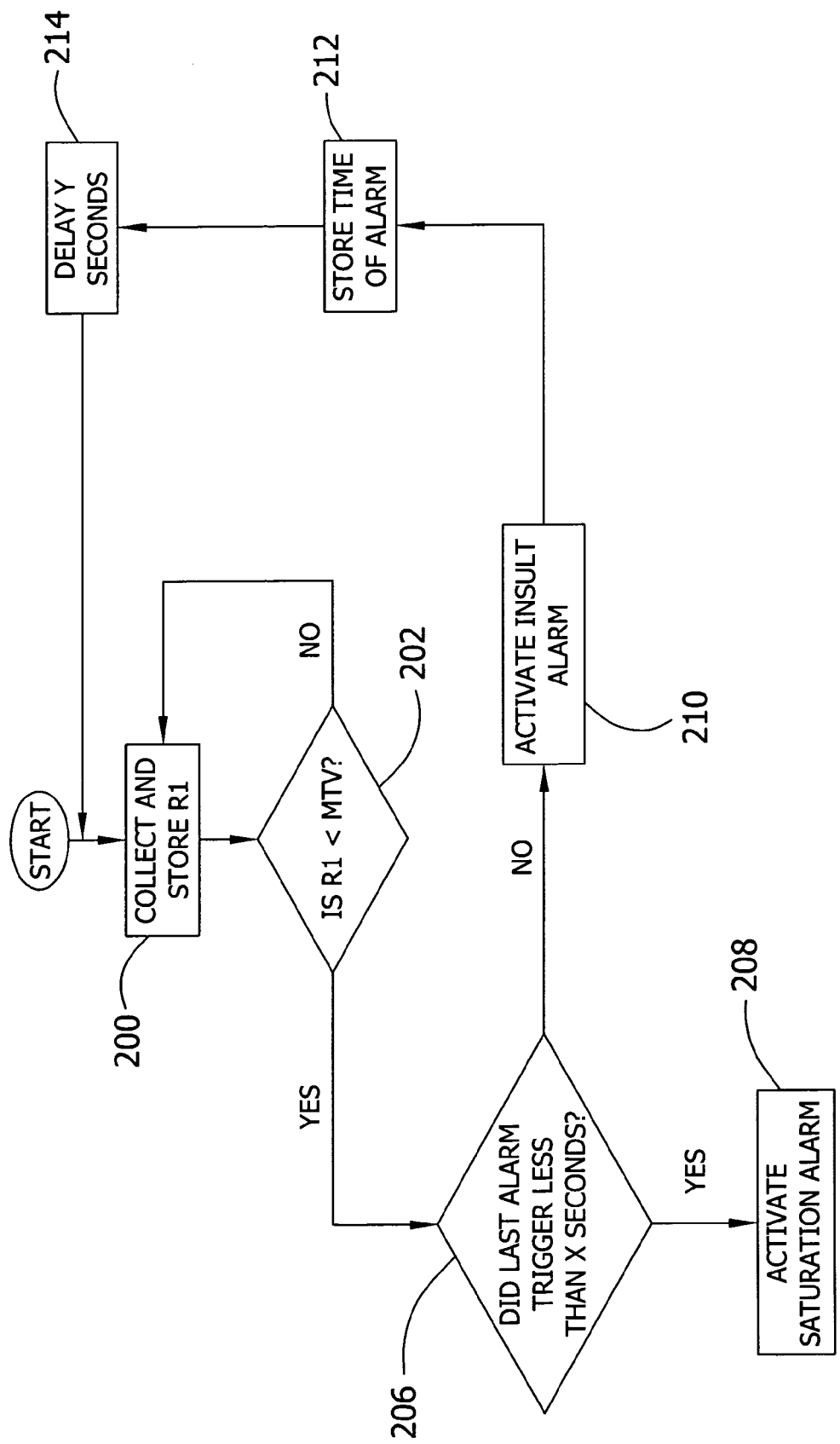
FIG. 20 is block diagram of another embodiment of the present invention illustrating instructions for the microprocessor for determining whether the pants are saturated and for allowing the resistance of the pants to stabilize after an insult.

In one example of the present embodiment, the analog output signal from the measuring device 85 is converted into a digital output signal and sent to the microprocessor 93, as illustrated in FIG. 7 and explained above. Referring to FIG. 20, the microprocessor 93, at instruction 200, collects and stores resistance value (R1) from the digital output signal.

Although this illustrated embodiment uses an all digital approach, it is understood that other examples may also use in part or in whole an analog approach, as would be generally understood by those in the art. At instruction 202 the microprocessor 93 compares the measured resistance value (R1) (broadly, the magnitude indicator value) to a magnitude threshold value (MTV) to determine whether the measured resistance is an indication of the presence of an insult (broadly, a first test). For example, the microprocessor 93 may be instructed to determine whether the resistance is less a magnitude threshold value of between about 30 KΩ and 90 KΩ, and more particularly about 55 KΩ. It is understood that this first test may be a test other than a magnitude threshold test without departing from the scope of this invention.

If the comparison is not indicative of the presence of an insult, then the microprocessor 93 is instructed to repeat the above steps and continue collecting, storing and comparing subsequent resistance values until the comparison of such to the magnitude threshold value is indicative of the presence of an insult. If the comparison is indicative of the presence of an insult, then the microprocessor 93 is instructed at 206 to determine whether the last insult alarm 95 (if there was one) was previously triggered within a preset time period. In one example, the microprocessor compares the amount of time that elapsed between the new insult and the previous insult and compares that amount to a time threshold value. For example, the time threshold value may be between 90 seconds and 300 seconds, and more particularly about 120 seconds. If the last insult alarm 95 was previously triggered within the preset time period, then the microprocessor 93 activates a saturation alarm at instruction 208. The saturation alarm is similar to the insult alarm 95 except that it notifies the caregiver and/or the wearer that the pants 20 are saturated and need to be changed. For example, the saturation alarm may play a different musical tune or make a different sound than the insult alarm which informs the caregiver and/or the wearer that the pants are saturated.

If the last insult alarm did not trigger less than a preset time period, then the microprocessor 93 activates the insult alarm 95 at instruction 210 to notify the caregiver and/or the wearer of the presence of an insult. During the activation of the insult alarm 95 the microprocessor 93 is instructed to cease determining the presence of an insult (e.g., comparing resistance values to the magnitude threshold value). The time of the alarm is stored in the microprocessor's memory at instruction 212, and the insult alarm 95 is activated for a period of time, for example between 15 seconds and 60 seconds. The period of time that the insult alarm 95 is activated may be a preset time built into the microprocessor 93 and/or the alarm. Alternatively, the monitoring system 70 may comprise of an alarm reset button (not shown), whereby the caregiver and/or the wearer may push the button to deactivate the alarm at anytime after activation thereof.

Figure 20A:
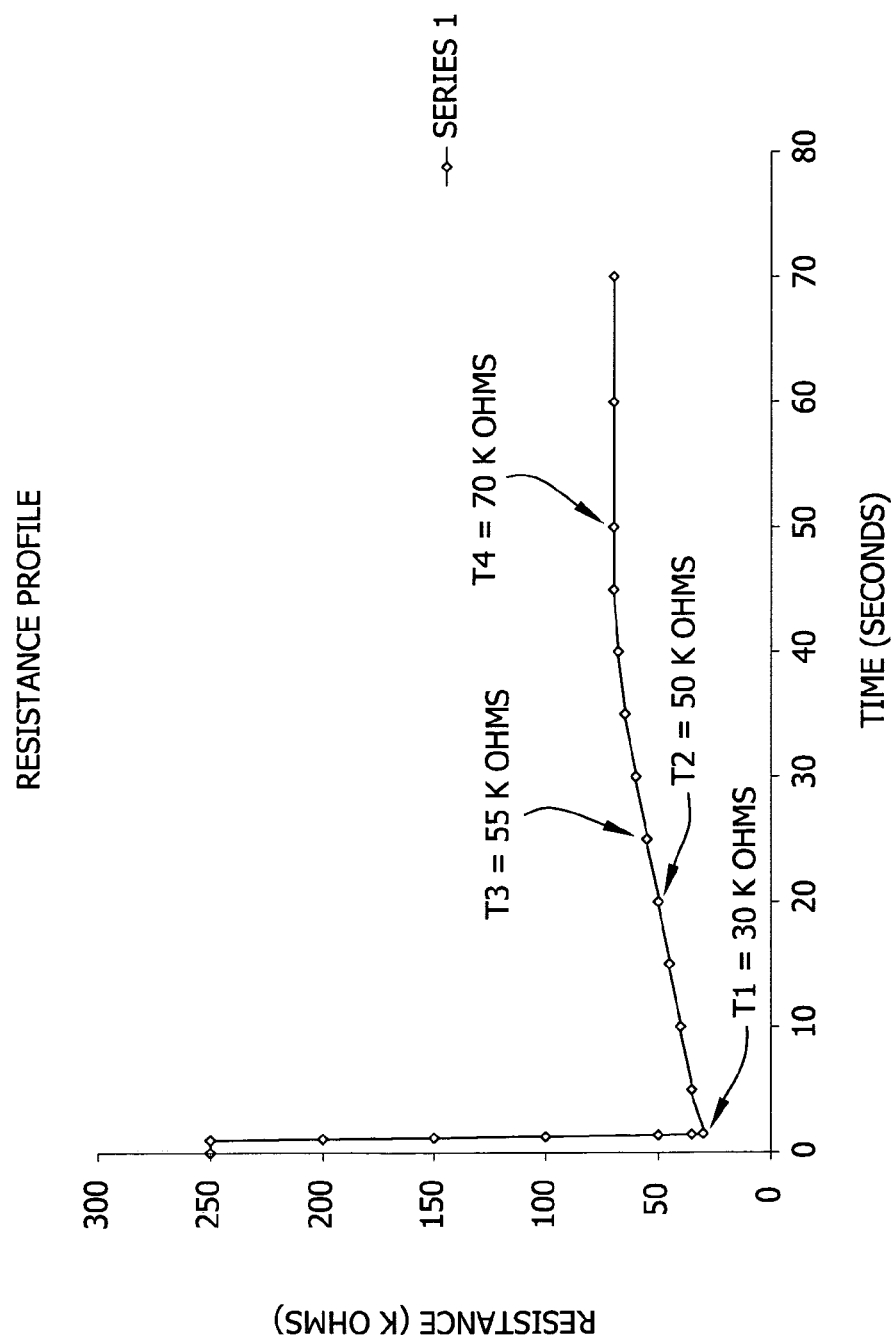
FIG. 20A is a graph illustrating an exemplary resistance profile of a pair of pants that has been insulted.

After the period of time of the activation of the insult alarm 95, the microprocessor 93 is instructed to delay further analysis for a period of time at instruction 214 before restarting its process of determining the presence of an insult (e.g, delay comparing resistance values to the magnitude threshold value). This delay function allows for the resistance profile of the pants to stabilize after the occurrence of an insult. The example shown in FIG. 20A illustrates the benefit of the delay. As shown in FIG. 20A, at time T1 (i.e., at about 1.5 seconds) the resistance of the pants drops to about 30 KΩ because of the presence of an insult. After the initial insult, the resistance slowly increases over time due to the insult being absorbed and mixing with the absorbent material of the pants. The insult alarm 95 is deactivated (either manually by the caregiver or user or by the microprocessor), at time T2 (e.g, at about 20 seconds). Without a delay instruction, the microprocessor 93 would begin comparing the resistance values to the threshold value immediately after deactivation of the alarm (e.g., at time 20 seconds). Assuming the magnitude threshold value is 55 KΩ, this would lead to either a false insult alarm or a false saturation alarm because the resistance of the pants at time 20 seconds is 50 KΩ. The resistance has not had ample time to increase to its stabilization point (around 70 KΩ in this example) and is still below the magnitude threshold value. With the present time delay embodiment of this invention, however, the determination of a subsequent insult by the microprocessor is delayed, for example, for 30 seconds after the deactivation of the insult alarm, thereby allowing the resistance of the pants to increase to its stabilization resistance (70 KΩ) at time T4 (i.e., 50 seconds). This delay function decreases the chances of the microprocessor 93 detecting a false insult or false saturation, thereby making the monitoring system 70 more accurate in detecting insults.

As an example, the microprocessor 93 may be instructed to delay for a preset time period between about 5 seconds and 600 seconds, and more particularly between about 10 seconds and about 60 seconds before restarting its determination the presence of an insult (e.g., comparing the present measured resistance to the magnitude threshold value). The time delay may be dependant on the length of the period of time of the activation of the alarm. For example, where the insult alarm 95 is deactivated manually by the caregiver and/or the wearer (such as by a push button) after 1 second, the time delay may be greater than if the alarm is deactivated after 30 seconds. This aspect of this embodiment of the invention is intuitive given the purpose of allowing the resistance of the pants to stabilize, as stated above.

It is understood that the delay function and the saturation detection function are not codependent functions of the monitoring system of the present invention, and an embodiment of the present invention may have one without the other without departing from the scope of this invention.

Figure 21:
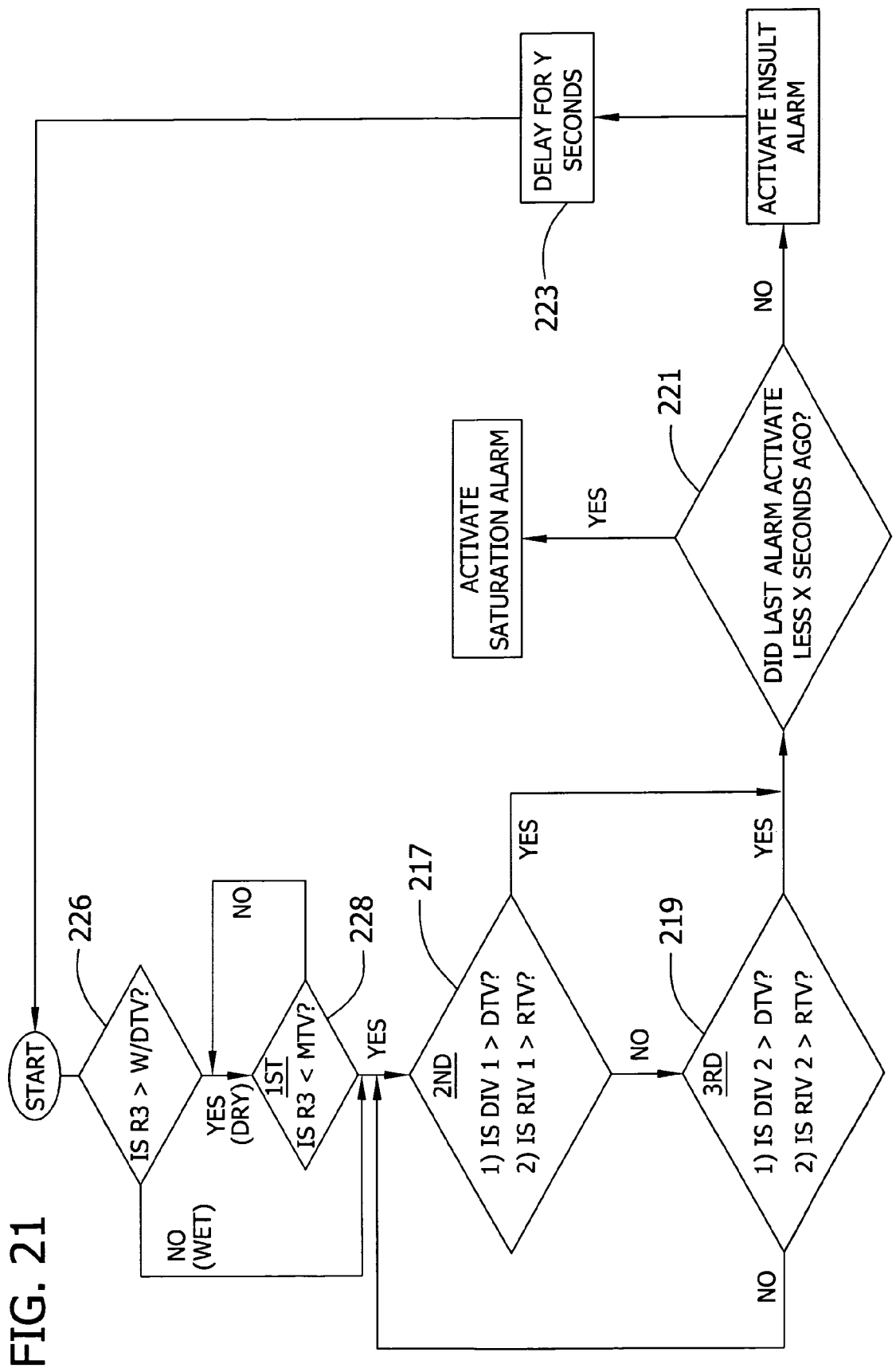
FIG. 21 is a block diagram of another embodiment of the present invention illustrating instructions for the microprocessor for determining whether the pants are dry, recently insulted, or saturated.
Figure 22:
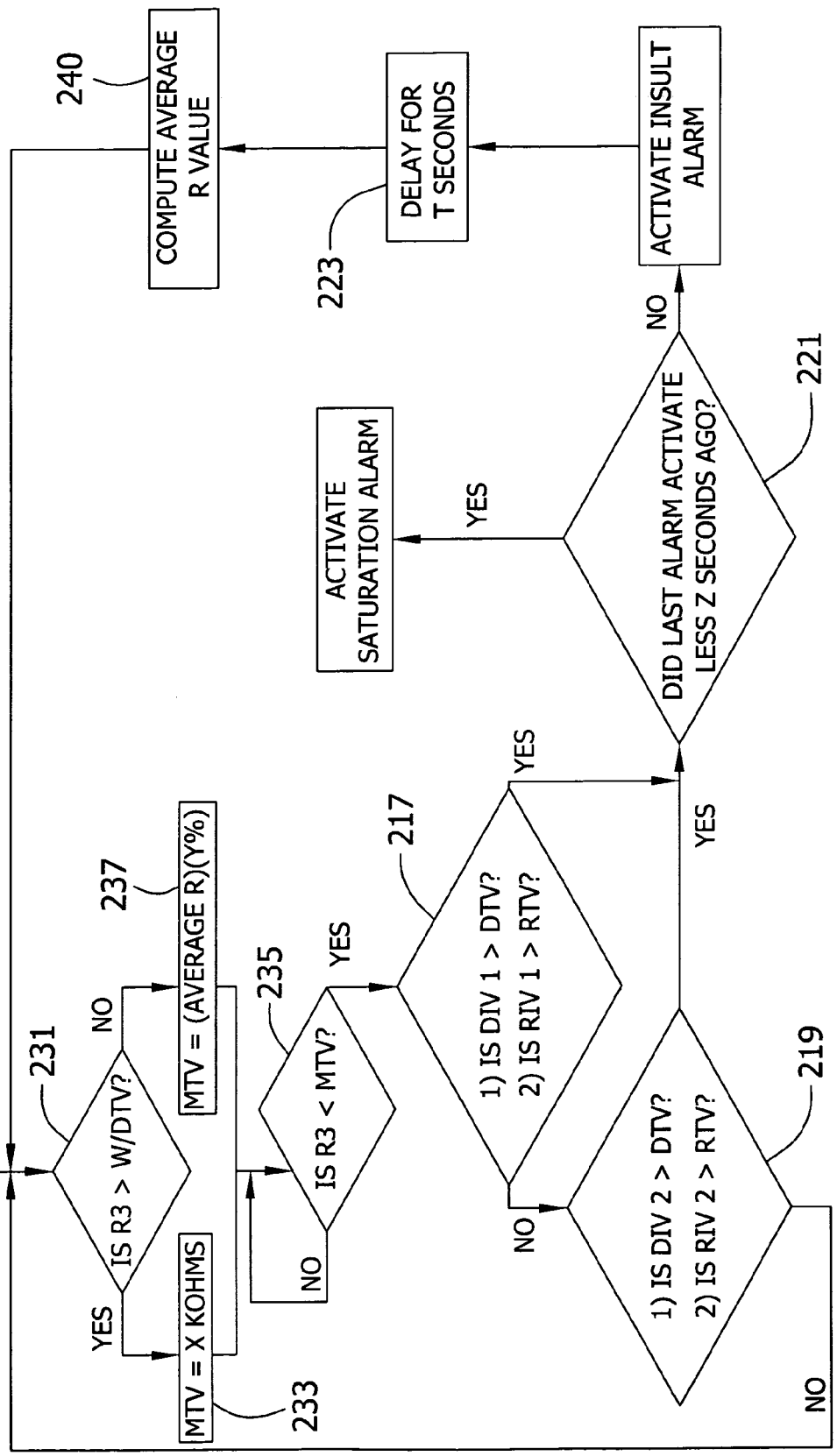
FIG. 22 is a block diagram of another embodiment of the present invention similar to the embodiment of FIG. 21 and further including instructions for calculating an average magnitude threshold value when the pants are recently insulted.
Figure 23:
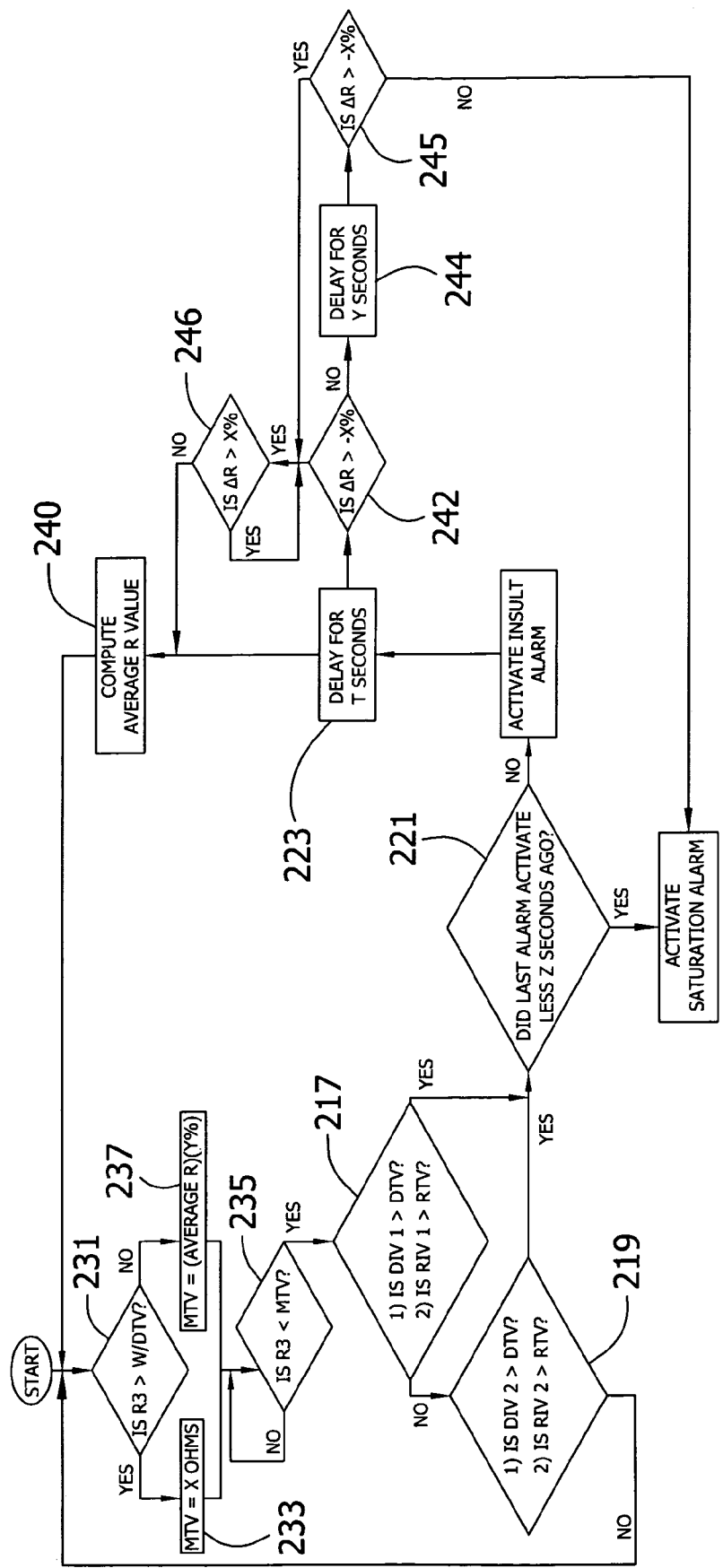
FIG. 23 is a block diagram of another embodiment of the present invention similar to FIG. 22 and further including instructions for delaying the calculation of the average magnitude threshold value until the resistance has stabilized.

Referring now to FIGS. 21-23, yet another embodiment of the monitoring system of the present invention substantially combines aspects of the percent difference embodiment illustrated in FIG. 9 and aspects of the rate of change embodiment illustrated in FIG. 11 as a second test (e.g., comparing a first difference indicator value—DIV 1 and a first rate indicator value—RIV 1, both of which are calculated using a third resistance and a second resistance, to respective threshold values—DTV and RTV) and a third test (e.g., comparing a second difference indicator value—DIV 2 and a second rate indicator value—RIV 2, both of which are calculated using a third resistance and a first resistance, to respective threshold values—DTV and RTV) as embodied in instructions 217 and 219, respectively. The monitoring system 70 further combines the saturation indicator and delay function embodiments illustrated in FIG. 20, as embodied in instructions 221 and 223, respectively.

In one example of this embodiment, illustrated schematically in FIG. 21, the microprocessor 93 is instructed at instruction 226 to compare a present resistance value (R3) (i.e., a magnitude indicator value) to a wet/dry threshold value (W/DTV) to determine if the pants have been previously insulted and are ready for subsequent sensing, or are still dry and have not been insulted. Although this illustrated embodiment uses an all digital approach, it is understood that other examples may also use in part or in whole an analog approach, as would be generally understood by those in the art. As an example, the microprocessor 93 may be instructed to determine if the resistance value is above, for example, 200 KΩ (wet/dry threshold value), which would indicate that the pants are dry and not previously insulted. If the comparison of the resistance value (R3) to the wet/dry threshold value (W/DTV) indicates that the pants are dry (e.g., R3 is greater than 200 KΩ), then the microprocessor 93 is instructed at instruction 228 to determine if the present electrical value compared to a magnitude threshold value is indicative of the presence of an insult (broadly, a first test). For example, the microprocessor 93 may determine if the present value of resistance is less than a magnitude threshold of between about 30 KΩ and 90 KΩ, and more particularly about 55 KΩ. If the comparison of the present resistance value to the magnitude threshold value is not indicative of the presence of an insult, then the microprocessor 93 continues collecting, storing and comparing resistance values to the magnitude threshold value looking for a comparison that is indicative of the presence of an insult. As illustrated by FIG. 21, the microprocessor 93 does not run the wet/dry test again, although doing so would not depart from the scope of this invention.

If the comparison of the resistance value (R3) to the wet/dry threshold value (W/DTV) at instruction 226 is not indicative of the pants being dry (i.e., it is indicative of the pants being wet), then the microprocessor 93 is instructed to skip the first test (embodied in instruction 228) of comparing the present electrical value to the magnitude threshold value. Typically, after the first insult (i.e., after the pants have been previously insulted), comparing the resistance of the pants 20 to a threshold value (i.e., performing the first test) is not beneficial because of the inaccuracies of the test after a first insult. However, this test may be beneficial when the pants are dry, which is why the test is performed when it is indicated that the pants are dry.

If either the comparison of the present resistance value to the dry/wet threshold value is indicative of the pants being previously insulted and ready to detect subsequent voids (e.g., R3<W/DTV) or the pants are dry (e.g., R3>W/DTV) and the comparison of the present value to the magnitude threshold value is indicative of the presence of an insult (e.g., R3<MTV), then the microprocessor runs the second test at the instruction 217 and possibly the third test at the instruction 219 to determine the presence of the insult. The second and third tests, which are explained in detail above, involve determining whether the percent difference and rate of change between the third and second values are indicative of the presence of an insult (e.g., DIV 1>DTV and RIV 1>DTV) and whether the percent change and rate of change between the third and first values are indicative of the presence of an insult (e.g., DIV 1>DTV and RIV 1>DTV). If the second test or the third test is indicative of the presence of an insult, then the microprocessor 93 is instructed to perform the saturation indication test at the instruction 221 and time delay function at the instruction 223 as explained above and illustrated in FIG. 20 and the present Figure. If neither the second test nor the third test is indicative of the presence of an insult, then the microprocessor 93 is instructed to run the second test and possibly the third test again with a new present resistance value (e.g., a fourth value), until a present value passes one of the tests.

Another example (FIG. 22) of this embodiment is similar to the example illustrated by FIG. 21. This example includes instructions for calculating a new magnitude threshold value to compare with the present resistance value if the microprocessor 93 determines that the pants 20 have been wetted, and are now detecting subsequent voids. Although this illustrated embodiment uses an all digital approach, it is understood that other examples may also use in part or in whole an analog approach, as would be generally understood by those in the art. As explained above, after the pants 20 have been wetted, the resistance of the pants when the resistance stabilizes is different from when the pants were dry, and therefore, using the fixed magnitude threshold value (e.g., 55 KΩ) may not be beneficial because it may falsely trigger the insult alarm 95. For example, after a first insult, the resistance of the pants may stabilize after the initial decrease to a resistance of 50 KΩ. If the microprocessor 93 solely uses a test with a magnitude threshold value being 55 KΩ, then the microprocessor will trigger the insult alarm even though a subsequent insult has not occurred. Calculating a new threshold based on the average resistance value of the pants after the first insult helps to prevent this occurrence of detecting false positives.

FIG. 22 illustrates schematically instructions for the microprocessor 93 for performing the above function of calculating a new magnitude threshold value. Although this illustrated embodiment uses an all digital approach, it is understood that other examples may also use in part or in whole an analog approach, as would be generally understood by those in the art. At instruction 231, the microprocessor compares the present resistance value (i.e., a third value) to a wet/dry threshold value (e.g., 200 KΩ) to determine if the pants are wet or dry, as explained above with reference to the example of FIG. 21. If the comparison indicates that the pants are dry (e.g., the third value is greater than 200 KΩ), then the microprocessor 93 is instructed at instructions 233 and 235, respectively, to set the magnitude threshold value to the predefined value (e.g., 55 KΩ) and compare the present resistance value to the threshold value to determine the presence of an insult.

If the comparison indicates that the pants have been wetted (e.g., the third resistance value is less than 200 KΩ), then the microprocessor 93 is instructed at instruction 237 and 235, respectively, to set an average magnitude threshold value as the magnitude threshold value and compare the present resistance value to the magnitude threshold value. The average resistance value at which the resistance in the pants has stabilized is calculated by the microprocessor 93 at instruction 240 after the activation of the insult alarm 95 and the delay period. At instruction 237, this average resistance value is multiplied by some percentage less than 100% to calculate the average magnitude threshold value. For example, the average resistance value may be multiplied by a percent between 50% and 95%, or more particularly, a percent between 80% and 90%.

If the comparison of the present resistance value with the averaged threshold value is indicative of the presence of an insult, then the subsequent instructions for the microprocessor are similar to the instructions of the previous example illustrated in FIG. 21, except that if the third test (e.g., the comparison of the percent difference and rate change between the third value and first value) is not indicative of the presence of an insult, then the microprocessor is instructed to return to instruction 231 and compare a new resistance value (e.g., a fourth value) to a wet/dry threshold value, and compare the new value to an appropriate threshold (i.e., either the fixed magnitude threshold or the average magnitude threshold).

Yet another example, illustrated schematically in FIG. 23, is similar to the example given in FIG. 22 and explained above. The present example further includes instructions for delaying the determination of the average magnitude threshold value until the resistance of the pants 20 has substantially stabilized after an insult. As explained above, after the pants 20 have been wetted by an insult, the resistance of the pants continues to generally climb over a period of time after the occurrence of the insult. Thus, it is advantageous to instruct the microprocessor 93 to wait to until the resistance of the article has substantially stabilized before instructed the microprocessor to calculate the average magnitude threshold value in order to calculate a more accurate average of the resistance.

In the present embodiment, change in the electrical property of the article 20 is monitored to determine if the electrical property has stabilized. For example, the monitored change may be a rate of change (determined, for example, in the manner described above), a percent change, or any other change that is generally indicative of the stabilization of the electrical property of the article. In the example illustrated in FIG. 23, after the activation of the insult alarm and the delay, the microprocessor 93 is instructed at instruction 242 to compare the percent change of the resistance of the pants to a lower preset percent (broadly, a lower preset value) to determine if the resistance is greater than the lower preset percent. The lower preset percent may be, for example, between −0.1% and −10%, or more particularly, about −5%. The microprocessor may calculate the percent change of the resistance in the same manner as it calculated the percent difference, as illustrated schematically in FIG. 8. That is, the microprocessor collects and stores a resistance value, delays, then collects and stores a subsequent resistance value. The latter value is subtracted from the former value and the difference is divided by the former value to get a percent change value. The resistance values collected after the activation of the insult alarm are used in this calculation. Other ways of calculating a percent change is within the scope of this invention.

If the resistance of the pants 20 is not increasing at a rate greater than the lower preset percent (e.g., less than −5%), then the microprocessor 93 is instructed to delay a preset time period at instruction 244. For example, the delay period may be between 60 seconds and 300 seconds, and more particularly about 120 seconds. After the time delay, the microprocessor 93 is instructed at 245 to compare a new percent change of the resistance that is calculated after the time delay of instruction 244 to the lower preset percent to determine if the resistance is greater than the lower preset percent. If the resistance is still not increasing at a rate greater than the lower preset percent, then the microprocessor 93 is instructed to activate the saturation alarm.

If the resistance of the pants is increasing at a rate greater than the lower preset percent (e.g., greater than −5%) either before or after the time delay of instruction 244, the microprocessor 93 is instructed at instruction 246 to compare the percent change of the resistance to an upper preset percent (broadly, an upper preset value) to determine if the percent change is less than the upper preset percent. The upper preset percent may be, for example, between 1% and 10%, and more particularly about 5%. If the percent change is less than the upper preset percent, then the microprocessor is instructed the instruction 240 to begin calculating the average resistance to be used in the average magnitude threshold value. That is, after the resistance has stabilized as indicated by the percent change being greater than the lower preset percent and less than the upper preset percent, the microprocessor 93 is instructed to begin sampling the resistance and using the sampled resistance for calculating the average resistance (e.g., average resistance). If the percent change is greater than the upper preset percent, then the microprocessor 93 is instructed to continue testing for when the percent change of the resistance is less than the upper preset percent, thereby signifying that the resistance has substantially stabilized. The computed average resistance is stored and used as needed.

It is understood that the exemplary values and range of values, given for the above tests/checks, including exemplary values given for the difference threshold value (DTV), the rate threshold value (RTV), the lower check value (LCV), the upper check value (UCV), the magnitude threshold value (MTV), the time threshold value for the saturation indicator embodiment, the time delay period, the wet/dry threshold value (W/DTV), and the upper and lower preset percents, are merely examples, and the values and time periods actually employed in the invention may change, depending on such variables as material characteristics of the pants (especially, at the monitoring area), the type of sensor used, the type of conductors used, location of the conductors within the pants, user preference, and any other variables affecting the indicator values and time periods used in the various tests.

When introducing elements of the present invention or the embodiments thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A method of detecting and communicating to a caregiver and/or a wearer the presence of an insult within an absorbent article, said method comprising:
    monitoring an electrical property of the article as the article is being worn by the wearer;
    determining the electrical property of the article at a first time, the electrical property being expressed as a first indicator value;
    activating an insult alarm to inform the caregiver and/or the wearer of the presence of an insult in the article when the first indicator value is indicative of an insult;
    determining the electrical property of the article after activating the insult alarm, the electrical property being expressed as a second indicator value;
    determining the second indicator value is indicative of the presence of a second insult within the article;
    determining the amount of time that elapsed between the activation of the alarm and the determination of the indication of the presence of the second insult;
    comparing the elapsed time to a time threshold value and activating either an insult alarm or a saturation alarm as a function of the comparison.

2. The method as set forth in claim 1 wherein the first and second indicator values are indicative of an insult when compared to a magnitude threshold value.

3. The method as set forth in claim 2 wherein the monitored electrical property of the article is resistance, and the first and second indicator values are indicative of an insult when the values are less than the magnitude resistance threshold.

4. The method as set forth in claim 2 wherein the monitored electrical property of the article is conductance, and the first and second indicator values are indicative of an insult when the values are greater than the magnitude conductance threshold.

5. The method as set forth in claim 1 wherein the time threshold value is between about 60 seconds and about 300 seconds.

6. The method as set forth in claim 1 wherein the time threshold value is between about 90 seconds and about 180 seconds.

7. The method as set forth in claim 1 wherein the time threshold value is about 120 seconds.

8. The method as set forth in claim 1 wherein determining the electrical property of the article after activating the insult alarm comprises determining the electrical property of the article a preset period of time after activating the sensor insult signal.

9. A method of detecting and communicating to a caregiver and/or a wearer the presence of an insult within an absorbent article, said method comprising:
    monitoring an electrical property of the article as the article is being worn by the wearer;
    determining the electrical property of the article at a first time, the electrical property being expressed as a first indicator value;
    activating an insult alarm for an alarm period to inform the caregiver and/or the wearer of the presence of a first insult in the article when the first indicator value is indicative of an insult;
    determining the electrical property of the article at a second time occurring at least a preset period after the end of the alarm period, whereby the preset period allows the electrical property to stabilize, the electrical property being expressed as a second indicator value;
    activating the insult alarm to inform the caregiver and/or the wearer of the presence of a second insult in the article when the second indicator value is indicative of an insult.

10. The method as set forth in claim 9 wherein the first and second indicator values are indicative of an insult when compared to a magnitude threshold value.

11. The method as set forth in claim 9 wherein said preset period lasts between about 5 seconds and 600 seconds.

12. The method as set forth in claim 9 wherein said preset period lasts between about 10 seconds and about 60 seconds.

13. The method as set forth in claim 9 wherein said preset period lasts about 15 seconds.

14. The method as set forth in claim 9 further comprising determining the amount of time that elapsed between the activation of the alarm and the determination of the indication of the presence of the second insult, and comparing the elapsed time to a time threshold value and activating either an insult alarm or a saturation alarm as a function of the comparison.

* * * * *

UNITED STATES PATENT AND TRADEMARK OFFICE
CERTIFICATE OF CORRECTION

| | |
|---|---|
| PATENT NO. | : 7,355,090 B2 |
| APPLICATION NO. | : 11/216977 |
| DATED | : April 8, 2008 |
| INVENTOR(S) | : Ales, III et al. |

It is certified that error appears in the above-identified patent and that said Letters Patent is hereby corrected as shown below:

Column 8, line 19, delete "permeable. wrapsheet" and insert therefor -- permeable wrapsheet --.

Column 11, line 55, delete "31%" and insert therefor -- 13% --.

Signed and Sealed this

Twenty-sixth Day of May, 2009

JOHN DOLL
*Acting Director of the United States Patent and Trademark Office*